(12) United States Patent
Mullaly et al.

(10) Patent No.: US 9,452,029 B2
(45) Date of Patent: Sep. 27, 2016

(54) FIXED HYBRID DENTAL ATTACHMENT DEVICE AND METHODS OF USING SAME

(71) Applicant: Zest IP Holdings LLC, Escondido, CA (US)

(72) Inventors: Scott Mullaly, San Marcos, CA (US); Christopher Michael Gervais, San Marcos, CA (US); James Irwin Johnson, Temecula, CA (US); Richard Robert Allen, Oceanside, CA (US); Theodore Matthew Powell, Escndido, CA (US)

(73) Assignee: ZEST IP HOLDINGS LLC, Escondido (CA)

( * ) Notice: Subject to any disclaimer, the term of this patent is extended or adjusted under 35 U.S.C. 154(b) by 0 days.

(21) Appl. No.: 13/711,515

(22) Filed: Dec. 11, 2012

(65) Prior Publication Data

US 2014/0162211 A1 Jun. 12, 2014

(51) Int. Cl.
| | |
|---|---|
| *A61C 8/00* | (2006.01) |
| *A61C 5/08* | (2006.01) |
| *A61K 6/04* | (2006.01) |
| *A61K 6/08* | (2006.01) |
| *A61C 13/265* | (2006.01) |

(52) U.S. Cl.
CPC ............ *A61C 8/0053* (2013.01); *A61C 5/08* (2013.01); *A61C 8/0048* (2013.01); *A61C 8/0054* (2013.01); *A61C 8/0068* (2013.01); *A61C 8/0089* (2013.01); *A61K 6/046* (2013.01); *A61K 6/08* (2013.01); *A61C 8/0001* (2013.01); *A61C 8/008* (2013.01); *A61C 13/2656* (2013.01)

(58) Field of Classification Search
CPC .. A61C 8/008; A61C 8/0053; A61C 8/0089; A61C 8/0068; A61C 8/0054; A61C 8/0062; A61C 5/08
USPC .................................................. 433/172–176
See application file for complete search history.

(56) References Cited

U.S. PATENT DOCUMENTS

| | | | |
|---|---|---|---|
| 711,324 A | 10/1902 | Lacy | |
| 3,514,858 A | 6/1970 | Silverman | |
| 3,732,621 A * | 5/1973 | Bostrom | A61C 8/0022 433/174 |

(Continued)

FOREIGN PATENT DOCUMENTS

| | | |
|---|---|---|
| EP | 501940 A1 | 9/1992 |
| WO | 95/18581 A1 | 7/1995 |

(Continued)

OTHER PUBLICATIONS

International Search Report and Written Opinion, PCT/US2012/041300, dated Sep. 20, 2012.

(Continued)

*Primary Examiner* — Yogesh Patel
(74) *Attorney, Agent, or Firm* — Procopio, Cory, Hargreaves & Savitch LLP; Noel C. Gillespie

(57) ABSTRACT

A hybrid, detachable dental attachment device comprising a cap for securing a dental appliance, a ring, and an abutment to attachment to a tooth root or implant. Also described herein are methods of securing a dental appliance in a subject's mouth by means of the dental attachment device. Further described herein is a dental attachment device for immediate load on a provisional denture and then incorporated into the final restoration.

15 Claims, 28 Drawing Sheets

(56) References Cited

U.S. PATENT DOCUMENTS

| | | |
|---|---|---|
| 3,787,975 A | 1/1974 | Zuest |
| 3,990,150 A | 11/1976 | Giovannini |
| 3,991,472 A | 11/1976 | Lukesch |
| 4,158,256 A | 6/1979 | Wiland et al. |
| 4,290,755 A | 9/1981 | Scott |
| 4,362,509 A | 12/1982 | Sulc |
| 4,431,416 A | 2/1984 | Niznick |
| 4,475,891 A | 10/1984 | Hader |
| 4,488,874 A | 12/1984 | Soifer et al. |
| 4,488,875 A | 12/1984 | Niznick et al. |
| 4,518,357 A | 5/1985 | Brinkmann et al. |
| 4,540,367 A | 9/1985 | Sulc |
| 4,547,156 A | 10/1985 | Hader |
| 4,626,213 A | 12/1986 | Shiner et al. |
| 4,645,453 A | 2/1987 | Niznick et al. |
| 4,657,510 A | 4/1987 | Gittleman et al. |
| 4,738,623 A | 4/1988 | Driskell et al. |
| 4,780,080 A | 10/1988 | Haris et al. |
| 4,793,808 A | 12/1988 | Kirsch |
| 4,832,601 A | 5/1989 | Linden et al. |
| 4,854,872 A | 8/1989 | Detsch |
| 4,907,969 A | 3/1990 | Ward |
| 4,932,868 A | 6/1990 | Linkow et al. |
| 4,934,935 A | 6/1990 | Edwards et al. |
| 4,957,438 A | 9/1990 | Bax |
| 4,988,297 A | 1/1991 | Lazzara et al. |
| 5,030,095 A | 7/1991 | Niznick et al. |
| 5,049,072 A | 9/1991 | Lueschen |
| 5,071,350 A * | 12/1991 | Niznick ............... 433/173 |
| 5,073,110 A | 12/1991 | Barbone |
| 5,092,770 A | 3/1992 | Zakula |
| 5,120,222 A | 6/1992 | Sulc |
| 5,194,000 A | 3/1993 | Dury |
| 5,195,891 A | 3/1993 | Sulc et al. |
| 5,211,561 A | 5/1993 | Graub |
| 5,302,125 A | 4/1994 | Kownacki et al. |
| 5,413,480 A | 5/1995 | Musikant et al. |
| 5,417,570 A * | 5/1995 | Zuest ............ A61C 13/2656 433/172 |
| 5,480,304 A | 1/1996 | Nardi et al. |
| 5,520,540 A | 5/1996 | Nardi et al. |
| 5,527,182 A | 6/1996 | Willoughby |
| 5,556,280 A | 9/1996 | Pelak |
| 5,564,924 A | 10/1996 | Kwan |
| 5,630,717 A | 5/1997 | Zuest |
| 5,636,989 A | 6/1997 | Somborac et al. |
| 5,639,239 A | 6/1997 | Earle |
| 5,678,997 A | 10/1997 | De Buck |
| 5,839,898 A | 11/1998 | Fernandes |
| 5,993,212 A | 11/1999 | Shiner |
| 6,030,219 A * | 2/2000 | Zuest et al. ............... 433/181 |
| 6,299,447 B1 * | 10/2001 | Zuest ............... A61C 8/0048 433/172 |
| 6,302,693 B1 | 10/2001 | Mena |
| 6,332,777 B1 | 12/2001 | Sutter |
| 6,500,003 B2 | 12/2002 | Nichinonni |
| 6,716,030 B1 | 4/2004 | Bulard et al. |
| 6,843,653 B2 | 1/2005 | Carlton |
| 6,981,871 B2 | 1/2006 | Mullaly et al. |
| 7,704,076 B2 | 4/2010 | Mullaly et al. |
| 8,128,403 B2 | 3/2012 | Karmon |
| D666,298 S | 8/2012 | Sibhatu et al. |
| 2005/0019730 A1 | 1/2005 | Gittleman |
| 2006/0275735 A1 | 12/2006 | Bulard et al. |
| 2008/0241790 A1 | 10/2008 | Gittleman |
| 2009/0155745 A1 | 6/2009 | Laux |
| 2009/0246734 A1 | 10/2009 | Bar Shalom |
| 2010/0055645 A1 | 3/2010 | Mullaly et al. |
| 2010/0105005 A1 * | 4/2010 | Bulloch ............... A61C 8/0048 433/173 |
| 2010/0129773 A1 | 5/2010 | Chen |
| 2010/0159420 A1 | 6/2010 | Mullaly et al. |
| 2010/0232869 A1 | 9/2010 | Ditzler et al. |
| 2010/0330536 A1 | 12/2010 | Mullaly |
| 2012/0045737 A1 | 2/2012 | Ang |
| 2012/0214128 A1 | 8/2012 | Collins et al. |
| 2012/0315599 A1 | 12/2012 | Mullaly |
| 2014/0162212 A1 | 6/2014 | Mullaly et al. |

FOREIGN PATENT DOCUMENTS

| | | |
|---|---|---|
| WO | 2004/004594 A1 | 1/2004 |
| WO | 2008040134 A1 | 4/2008 |
| WO | 2008/079699 A2 | 7/2008 |
| WO | 2009/156601 A2 | 12/2009 |
| WO | 2010/025034 A1 | 3/2010 |
| WO | 2012/170663 A1 | 12/2012 |

OTHER PUBLICATIONS

Langer, et al., "Tooth-supported telescopic prostheses in compromised dentitions: A clinical report," The Journal of Prosthetic Dentistry, 84(2); 129-132 (2000).

Response to Written Opinion of the International Search Authority in PCT/US2012/041300.

EP Communication Pursuant to Article 94(3) EPC, dated Mar. 19, 2014 for EP Application No. 03763001.9-1659 (5 pages).

International Search Report and Written Opinion for PCT/US2013073145, dated Mar. 19, 2014 (8 pages).

* cited by examiner

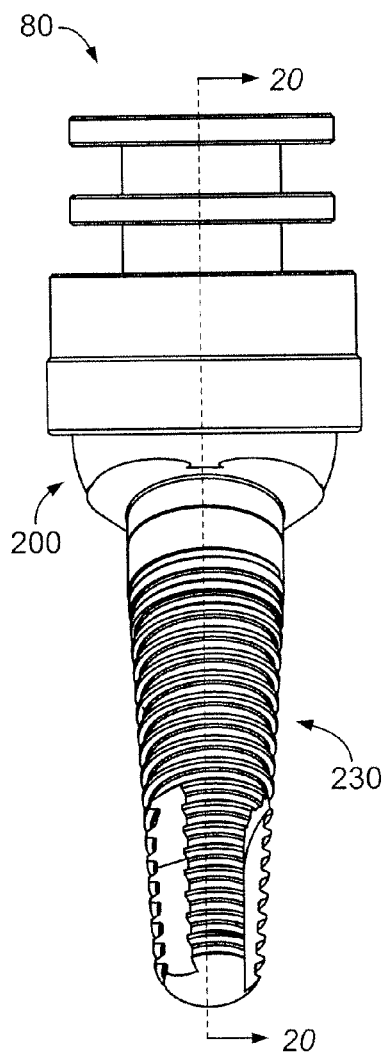
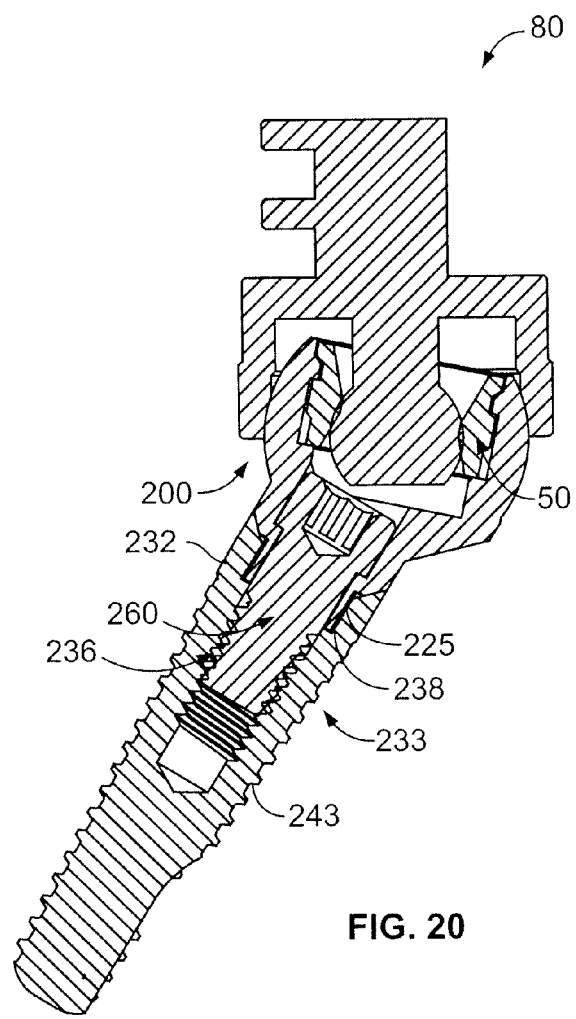
FIG. 19
FIG. 20

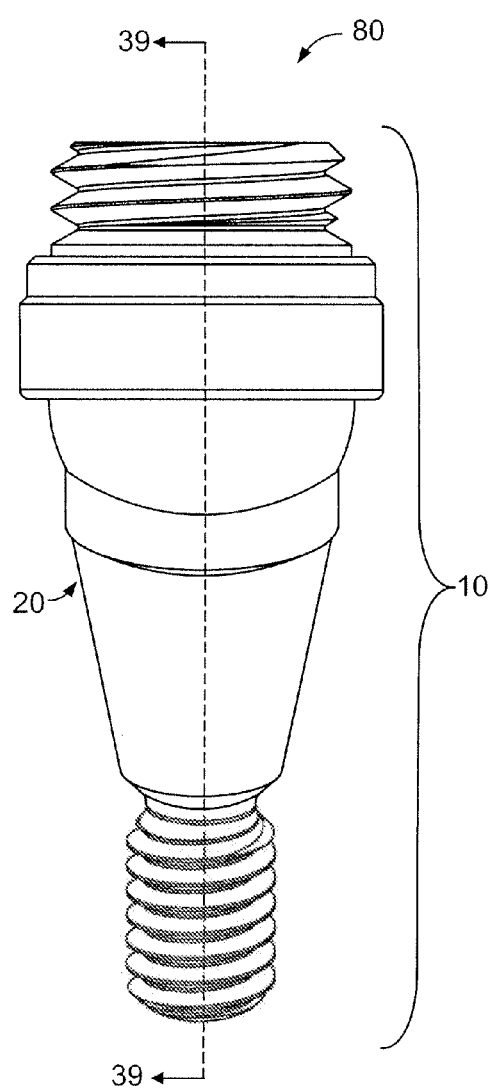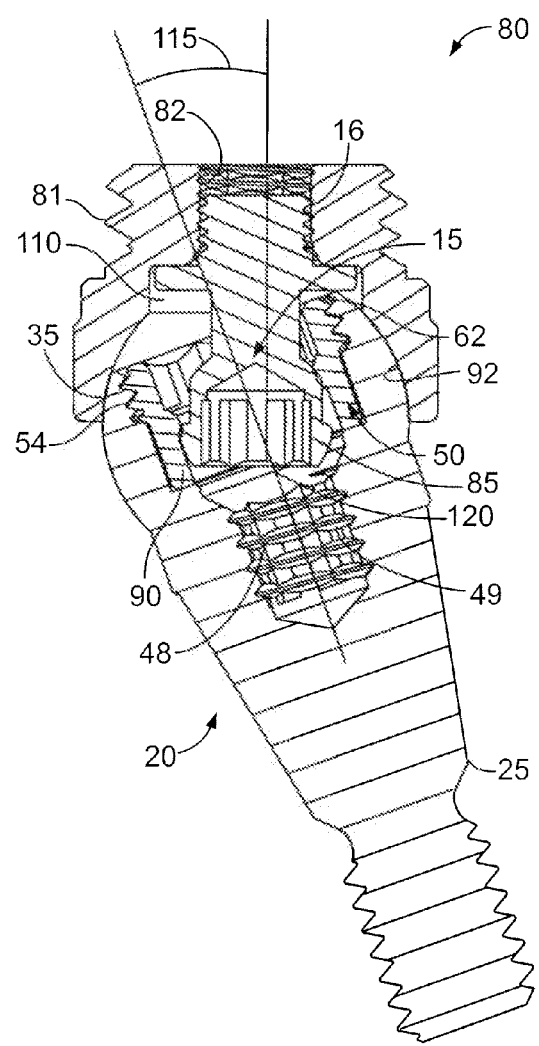
FIG. 38
FIG. 39

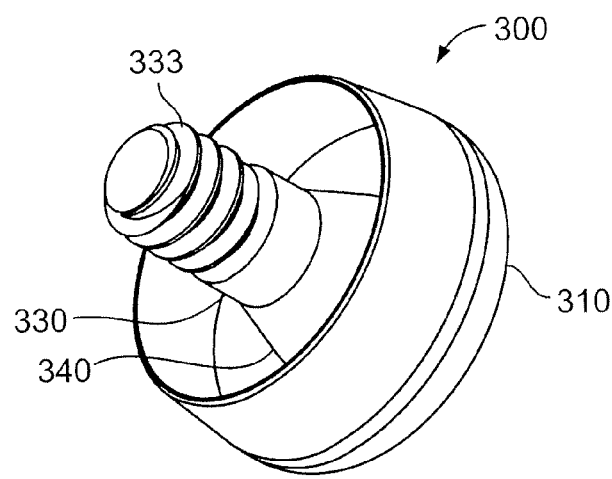
FIG. 44
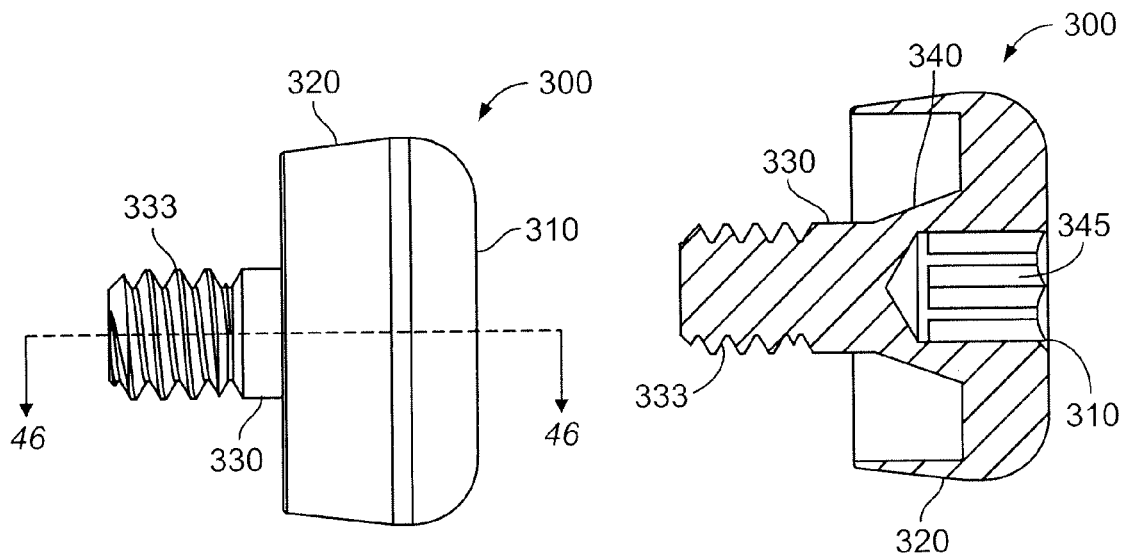
FIG. 45
FIG. 46

FIXED HYBRID DENTAL ATTACHMENT DEVICE AND METHODS OF USING SAME

FIELD

The present invention relates to a hybrid dental attachment device that functions similar to a fixed attachment system yet can be removed by a dental professional using a special tool. The invention further relates to methods of using the hybrid device.

BACKGROUND

A denture is a prosthetic device constructed to replace some or all of the missing natural teeth in a patient's mouth. There are two types of dentures: a partial denture and a complete denture. The partial denture replaces a few missing teeth, while the complete denture substitutes the entire maxillary and/or mandibular arch. Dentures can be secured to dental implants or non-vital tooth roots in the mouth of a patient using either a removable or fixed attachment system. In general, a removable denture is designed and fabricated to be attached to dental implants and removed by the patient, whereas a fixed denture is attached to dental implants using cement or screws and can only be removed by a dental care provider. Accordingly, the retention forces of fixed dentures attached to dental implants are quite high and may, in some cases, be at or near the physical breaking points of the various components (e.g., in excess of 100 pounds of force). In contrast, retention forces for patient-removable prostheses, whether with ball attachments or Locator® attachments (Zest Anchors, Inc., Escondido, Calif.), range from about 1 to about 7 pounds.

Both the removable and fixed implant supported dentures have their advantages and disadvantages. Common advantages for both the removable and fixed dentures include: proper chewing, protection of the gums, and improvement in speech and aesthetics. Removable dentures are less costly and allow for easier cleaning to promote oral hygiene on a daily basis. However, they lack the feel of natural teeth and require more maintenance, e.g., replacement and/or adjustment of attachments and attachment components. In contrast, fixed dentures feel more like natural teeth and distribute occlusal load onto the implant and onto the jaw bone, which can be beneficial to the maintenance of the bone ridge height and thickness, bone quality, and oral and facial aesthetics. Fixed dentures also allow less food entrapment and less maintenance. Nevertheless, fixed dentures are more expensive and more difficult to maintain when comprehensive cleaning is required.

Conventional fixed dental implant attachment systems generally have higher treatment costs and involve more complicated procedures. The cost of components and laboratory fees contribute, in part, to high treatment costs that restrict access of such conventional fixed attachment systems. At the same time, complicated techniques, such as accommodating implant angulations, verification of try-ins, and difficulty with administering cement and/or screws, requires highly skilled dental care providers, which further adds to the high cost of treatment. Likewise, maintenance of conventional fixed attachment systems require time consuming procedure and high cost as the system and/or system components are typically damaged and require repair and/or removal and replacement at recall appointments.

Accordingly, there is a need in the art for a simple, low cost, screwless, cementless, fixed dental implant attachment system that is detachable by the dental care provider, but at the same time provides the benefits of a fixed dental attachment system. Disclosed herein is a unique, simple, lower cost, fixed but clinically detachable device for those patients who want the advantages of a "fixed" implant supported denture but cannot afford the current higher end options, and an entry point allowing less experienced dentists to perform fixed restorations due to an easier restorative procedure. Further described herein is a dental implant attachment device that can provide immediate load (function), through components that can be easily used with the provisional denture and then incorporated into the final restoration.

SUMMARY OF THE INVENTION

Described herein is a fixed dental attachment device, a dental attachment assembly, and methods of securing a dental appliance in a subject's mouth using the same. In one embodiment, a dental attachment device comprises a cap for securing a dental appliance, a retainer ring, and an abutment. The cap may be integral with a dental appliance, such as a full denture, overdenture, or partial denture. Depending on the extent of the dental appliance, one or more abutments may be present in the subject's mouth with corresponding caps being integral with the dental appliance.

Though the fixed abutment and denture cap have internal features generally consistent with the geometry of O-ring or O-ball attachment systems, it is substantially differentiated in two principal ways. First, the fixed abutment is designed to rigidly connect the prosthesis (i.e. denture) to dental implants and remain in place with only periodic removal (i.e. once or twice a year for hygiene maintenance) by a clinician with use of a tool specifically designed for that purpose. Conversely, O-ring or O-ball attachment systems provide substantially less retentive force and are designed to be used with a removable prosthesis, allowing the patient to easily take out and replace their denture on a routine (i.e., daily) basis.

Second, the fixed abutment system attaches the prosthesis directly to a dental implant thereby transferring all mastication loads to a series of implants that are integrated in the patient's jaw. The O-ring or O-ball systems are solely intended to provide resilient retention of the denture in the mouth with the prosthesis seating directly on the soft tissue, or gingiva, which absorbs substantially all intra-oral forces such as those from mastication. This is an important distinction as tissue borne dentures are typically more uncomfortable for a patient because the prosthesis can compress, abrade, and pinch the gums during chewing function.

An example of an O-ring attachment systems is described in U.S. Pat. No. 6,302,693 to inventor Mena. Mena discloses a standard O-ring attachment system comprising a ball and socket secured by an O-ring. However, Mena differentiates between existing O-ring attachment systems by placing the socket in the abutment and the ball in the prosthesis. This arrangement allows the prosthesis to engage closer to the bone and surrounding tissue, thereby lowering the stress point. Nevertheless, Mena's attachment system is still fundamentally a conventional, removable O-ring attachment system.

In one embodiment, the present invention relates to a dental attachment device, comprising: (a) a cap for securing a dental appliance having an open end and an inner cavity forming a concave annular wall, and a first attachment portion; (b) an abutment comprising an upper portion and a second attachment portion, the upper portion having a convex outer surface and an open end; and (c) a removable ball having an upper end and a head portion, the removable ball is positioned between the cap and the abutment, wherein the head portion is retentively engaged in the open end of the abutment and the upper end engaged in the cap, wherein the engagement of the removable ball and the abutment has a retention force in an amount sufficient for rigid attachment of the device to the appliance and to prevent, inhibit, or reduce the risk of removal of the device by a patient using the device.

The retention force may vary and in certain embodiments is at least 15 pounds; or about 15 to about 75 pounds; or about 20 to about 50 pounds; or about 30 to about 40 pounds as measured using a tensile force measurement device (Instron Corp. Model 8841) on a single abutment. In another embodiment, the device further comprises a ring seated in the open end of the abutment and surrounding the head portion of the removable ball.

In another embodiment, the present invention relates to a method for securing a dental appliance in a subject's mouth by a dental professional, comprising the steps of: (a) positioning an abutment by an attachment portion into an existing non-vital tooth root, implant, mini-implant, or intermediary abutment, the abutment further comprising an upper portion, the upper portion having a convex outer surface and an open end; (b) positioning a removable ball into the open end of the abutment, the removable ball having an upper end engaged in a cap (that is integral with a dental appliance) and a head portion, the head portion retentively engaged in the open end of the abutment; and the cap is engaged over the outer upper surface of the abutment for securing the dental appliance, wherein the engagement of the removable ball and the abutment has a retention force in an amount sufficient for rigid attachment of the abutment, ball, and cap to the appliance and to prevent, inhibit, or reduce the risk of removal of them by the patient. In certain embodiments, the dental professional secures a plurality of dental attachment devices in the mouth of the subject, and wherein the retention forces vary between and among the plurality of devices.

Other embodiments, objects, features, and advantages will be set forth in the detailed description of the embodiments that follow and, in part, will be apparent from the description or may be learned by practice of the claimed invention. These objects and advantages will be realized and attained by the devices, assemblies, and methods described and claimed herein. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

BRIEF DESCRIPTION OF THE DRAWINGS

The details of the present invention, both as to its structure and operation, may be gleaned in part by study of the accompanying drawings, in which like reference numerals refer to like parts, and in which:

FIG. 19 is a side view of the assembled dental attachment device with a 20° pre-angled abutment of FIG. 16
FIG. 20 is a cross-sectional view of FIG. 19.
FIG. 38 is a side view of the assembled dental attachment device of FIG. 25 with a divergence between the cap and abutment.
FIG. 39 is a cross-sectional view of FIG. 38.
FIG. 44 is a perspective view of a healing cap.
FIG. 45 is a side view of FIG. 44.
FIG. 46 is a cross-sectional view of FIG. 45.

DETAILED DESCRIPTION

Figure 1:
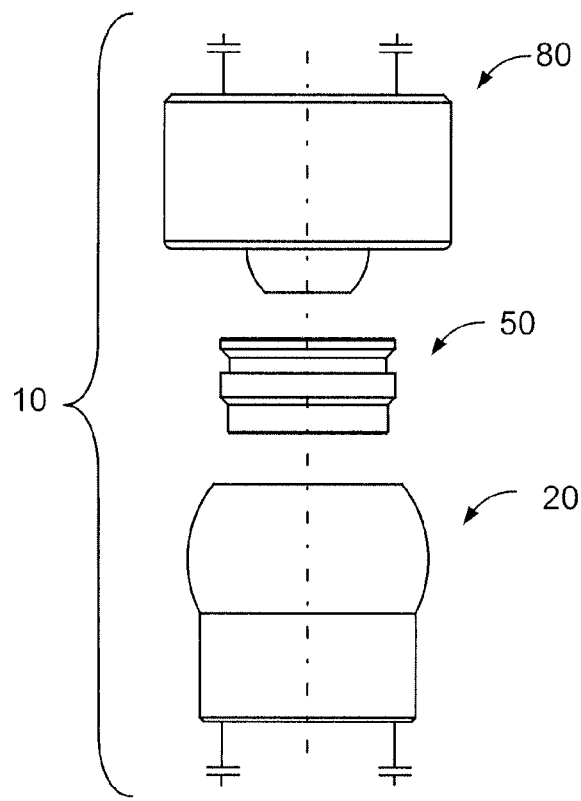
FIG. 1 is an exploded view of the dental attachment device.

While the present invention is capable of being embodied in various forms, the description below of several embodiments is made with the understanding that the present disclosure is to be considered as an exemplification of the claimed subject matter, and is not intended to limit the appended claims to the specific embodiments illustrated and/or described, and should not be construed to limit the scope or breadth of the present invention. The headings used throughout this disclosure are provided for convenience only and are not to be construed to limit the claims in any way. Embodiments illustrated under any heading may be combined with embodiments illustrated under any other heading.

In certain embodiments, the present invention relates to a dental attachment device comprising a cap, a ring, and an abutment. The cap secures a dental appliance and has an open end and an inner cavity that forms an annular wall surrounding a retention head. The abutment comprises an upper portion having a convex outer surface. The convex outer surface has an open end and an internal socket for receiving the ring and engaging the retention head. The dental appliance may be secured in a subject's mouth by attaching the abutment into an existing non-vital tooth root or implant, aligning the cap over the abutment, and engaging the retention head through the ring and into the socket of the abutment thereby securing the cap (and dental appliance) onto the abutment.

The fixed abutment and denture cap described herein have internal features generally consistent with the O-ring or O-ball attachment systems, however, it is substantially differentiated in two principal ways. First, the fixed abutment is designed to rigidly connect the prosthesis to dental implants and remain in place with only periodic removal by a clinician with use of a tool specifically designed for that purpose. Conversely, O-ring or O-ball attachment systems provide substantially less retentive force and are designed to be used with a removable prosthesis, allowing the patient to easily take out and replace their denture on a daily basis. Second, the fixed abutment system attaches the prosthesis directly to a dental implant thereby transferring all mastication loads to a series of implants that are integrated in the patient's jaw. In contrast, the O-ring or O-ball systems are solely intended to provide resilient retention of the denture in the mouth with the prosthesis seating directly on the soft tissue, or gingiva, which absorbs substantially all intra-oral forces such as those from mastication. This is an important distinction as tissue borne dentures are typically more uncomfortable for a patient because the prosthesis can compress, abrade and pinch the gums during chewing function.

The present invention further contemplates a kit comprising one or more hybrid fixed dental attachment devices and one or more tools designed for periodic removal.

As detailed further below, in one aspect of the present invention exemplified in FIG. 25, the design and materials of removable ball 15 and ring 50 are optimized to be retained or affixed to abutment 20 to provide a retention force sufficient for the device 10 to be secured against movement or disengagement when subjected to the normal mastication loads applied across the dental arch. Such retention force also makes removal of the denture by the patient impractical requiring a clinician to use a specifically designed tool to disengage removable ball 15 and cap 80 from abutment 20. Accordingly, the retention force is an amount sufficient to handle the mastication loads of conventional fixed devices yet prevent, inhibit, or reduce the risk of removal of the device by the patient.

More specifically, the retention force can vary depending on patient needs. In one embodiment, the force ranges from about 10 to about 75 pounds as measured using a tensile force measurement (Instron Corp. Model 8841) device per abutment. In other embodiments, the force ranges from about 15 to about 50 pounds, or from about 20 to about 45 pounds, or from about 25 to about 40 pounds, or from about 30 to about 35 pounds. In yet another embodiment, the force is about 15 pounds, or about 20 pounds, or about 25 pounds, or about 30 pounds, or about 40 pounds, or about 45 pounds, or about 50 pounds, or about 55 pounds, or about 60 pounds, or about 65 pounds, or about 70 pounds, or about 75 pounds.

The present invention, therefore, provides a system that has the ability to adjust the amount of retention force based on the large variation of patients and clinical conditions. For example, where loading is applied to a cantilevered area of the restoration, the force of retention should be proportionally larger to ensure that the restoration does not come unseated. Further, the desired retention force can also vary based on the size of the individual and the amount of bite force that a particular individual can generate. In some cases, with low bite forces or no cantilever, it is desirable to have the retention force lower so that the restoration is less difficult to seat and remove when the clinician performs maintenance.

In non-cantilevered applications, the only significant tensile (retention) force that the assembly must withstand is the force to remove the denture from the mouth by the patient. Forces in the range of 10 to 15 pounds per abutment will be sufficient to keep the prosthesis in place in this situation. Considering the prosthesis as a beam (denture) supported by columns (abutments) on either end, the majority of forces seen at the abutment/cap junction will be compressive forces bearing towards the abutment and implant.

For cantilevered situations, the prosthesis can be considered as a beam (denture) overhanging a column (abutment) on one end and fixed to a column (abutment) on the opposite end. This "fixed" end can resist a certain application of a tensile load. When the mastication force is applied on the free or overhanging end of the beam, the closest column acts as a pivot point, causing the "fixed" end to be subjected to a tensile load. While there are a number of factors that define the resulting tensile force, the system acts, in general, according to the principles of a lever or moment arm which creates a mechanical advantage. The force applied on one end of a pivot point multiplied by the distance from the application of force to the pivot point will be equal to the distance from the pivot point to the reaction point (on the other side) multiplied by the reaction force (e.g., $F1 \times D1 = F2 \times D2$). Based on this principle, it generally holds that if the resistance to tensile (removal force) is, for example, 60 pounds, up to a 30 pound load may be applied to a cantilever that is twice as long as the span between the pivot point and the "fixed" end without overcoming the amount of retention. The possible clinical situations are infinite based on patient bite strength and ratio between the cantilever span and the supported span of the prosthesis. It is estimated from literature that high posterior bite forces will be in the range of 50-80 pounds. In such a case, the cantilever should have a length approximately equal to the length from the pivot point to the "fixed" end so that the fixed point is not overcome by the reaction load and becomes unseated during function. In patients with lower bite force or in an area of the mouth more anterior, where reduced leverage of the jaw muscles creates lower bite forces, the cantilever may be extended one to two times the length of the supported section or more.

To determine the retention forces of the devices disclosed herein, Applicant performed various tests as follows:

Most of the testing was conducted in cantilevered conditions with the understanding that retention forces less than 30 pounds can be achieved by reducing the sharpness of the edge on the retention ball and/or reducing the amount of interference between the ball and the ring. Accordingly, a retention force of about 60 pounds or greater was the focus of testing. Further, in many cases, an understanding of the mechanical advantage of the lever arm allowed testing for the direct pull off force on a single abutment, so the device was tested in this manner.

The retention force was measured using an Instron Dynamight force testing machine (Instron Corp. Model 8841) with load cell and digital controller. The cap is seated on an abutment using a specified compressive load as measured on the force testing machine. For a single abutment, the cap was pulled off of the abutment by application of a tensile load. In a cantilever situation, a compressive load was applied to the distal end of the cantilever until the "fixed" point became unseated. The peak load to unseat the cap was measured at known cantilever and supported lengths. By making this measurement, actual values were measured compared with the calculated values of a simplified mechanical advantage lever problem.

Figure 52:
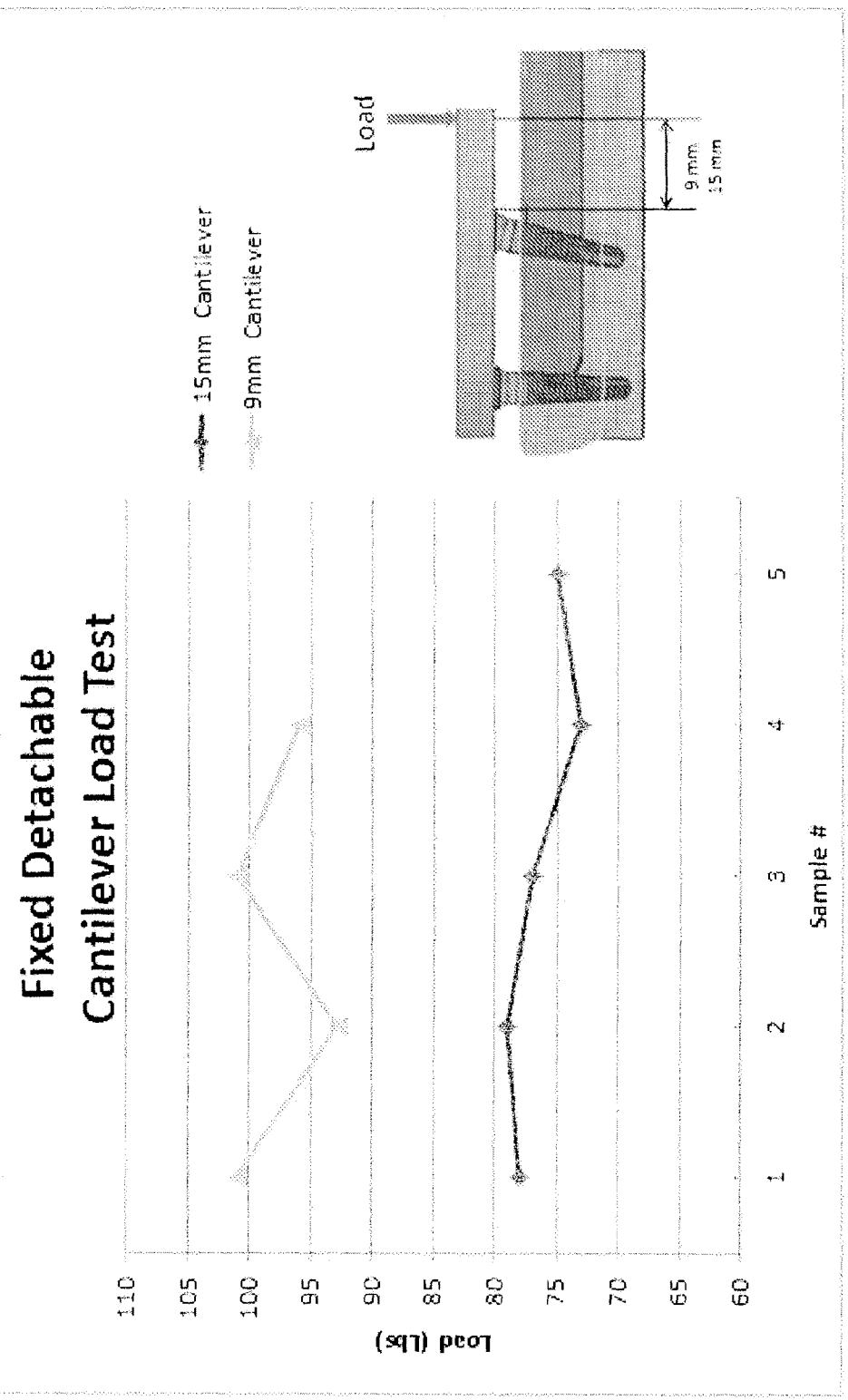
FIG. 52 is a graphic representation of the retention force of FIG. 25 in cantilever situation

In total, seventy-seven (77) tests were conducted on various conditions under the cantilever loading situation. This included variations in retention ball and ring configurations and at various cantilever lengths or, more specifically, various ratios of cantilever to supported lengths. FIG. 52 is a graphic representation of the retention force of the device in cantilever situation.

The assembly of FIG. 1 was found to provide sufficient retention in non-cantilevered situations. In cantilever situations, the assembly of FIG. 25 was found to provide the necessary retentive strength to maintain the prosthesis. The sharp edge on the retention ball bit into the plastic ring and increase the retention strength. Removal of the ball in this case caused permanent damage to the ring, requiring the ring to be replaced prior to reseating of the prosthesis.

Such test data establish that the range of retention necessary to securely attach a non-cantilevered fixed hybrid denture is approximately 15 to 20 pounds per abutment. This retention level secures a fixed denture against movement or disengagement when subjected to the normal mastication loads applied across the dental arch. This range of retention also makes removal of the denture by the patient impractical requiring a clinician to use a specifically designed tool to disengage the prosthesis. Although the embodiments of FIGS. 1 and 25 were tested, the retention forces apply to the other embodiments disclosed herein.

The retention necessary to secure a cantilever fixed denture (where teeth are distal to the most posterior implant) can range from 30 to 35 (and could be upward of 50 to 60 pounds) pounds per abutment based on empirical studies of cantilever forces as discussed above. The increase in retention is required to counteract the tensile forces that are imparted on the anterior abutments by the mastication forces applied to the cantilever or free end portion of the denture. This range of retention continues to make patient removal impractical and requires that a clinician use a special tool to disengage the prosthesis.

In certain embodiments of the present invention, there are two design features of the fixed hybrid attachment system that work together to achieve the above-referenced retention levels. While detailed more specifically in connection with FIGS. 25 to 37, the first feature achieves retention through interference with a ring engaged in the abutment with a barb-shaped removable ball, which is attached to the open-end of the cap. The retention force can be varied by using one of two-barb shaped removable ball configurations, one having a rounded or radius edge and the other having a sharp edge. The rounded or radius edge barb creates the sufficient retention for non-cantilever cases whereas the sharp edge barb provides the additional retention necessary for cantilevered cases by creating a greater interference and resistance to removal with the engaging side of the ring. The ring may be comprised of polyether ether ketone (PEEK) or other plastic.

The second retention feature comprises a metal-to-metal interface between the upper end of the abutment and the inner diameter of the cap. The mating of these two surfaces results in a galling or press fit effect that creates retentive force between the components. The metal-to-metal interference and resulting retention is achieved by the compressive biting force applied at the time of seating the prosthesis and caps on the abutments and then further through the continuous mastication forces imparted by the patient. The two retention features described above are designed to work alone or in conjunction with each other to achieve the final retention level needed for either cantilevered or non-cantilevered cases.

As mentioned, the hybrid devices of the present invention are to be removed by dental professionals using a special tool. In one embodiment, the tool is a pry tool that engages both the anterior and the posterior portions of the denture. By using the posterior abutments as a pivot point, the tool puts a compressive load on the cantilever. It also engages the anterior portion of the denture and pulls up on the underside of the prosthesis, applying a tensile load to the abutment at the "fixed" point. The tool has a long lever arm to allow the clinician to apply a reasonable amount of force to overcome the retention force on the anterior abutment(s). The tool can engage the underside of the prosthesis in a variety of ways, including but not limited to, having a bar that slides under the bottom of the denture. It can also have a flexible cord with sufficient tensile strength. This cord can be passed underneath the prosthesis and secured to the tool, creating a loop. This loop or bar will then pull up on the denture, helping to achieve a secure release. Once the front is released, the tool can be moved to the other side and used to pry up the connection in the posterior in the same way.

FIG. 1 illustrates one embodiment of the dental attachment device for securing a dental appliance in the mouth of a subject. FIG. 1 is an exploded view of the dental attachment device 10 comprising: a cap 80 for securing in the dental appliance, an abutment 20 for attachment to a non-vital tooth root, implant or the like, and a retainer ring 50. The cap 80 engages with the abutment 20 and ring 50 as indicated by the center line of FIG. 1 to secure a dental appliance in the mouth of a subject. The abutment 20 may be adapted to be compatible with commercially available implants, such as the Astra implant (Astra Tech Inc., Waltham, Mass.), Brånemark implant (Nobel Biocare, Zurich, Switzerland), and the Straumann implants (Straumann USA LLC, Andover, Mass.), or configured as a tooth root abutment, mini-implant, or in a configuration that can be adapted to an intermediary abutment, which would be secured to a dental implant. Likewise, the cap 80 may be designed to integrate in a dental appliance by means of, for example but not limited to, a post, a screw, or an adhesive, such as acrylic, bisacrylic, or other dental cements. Dental appliances include, but are not limited to, full dentures, overdentures, and partial dentures. Thus, depending on the extent of the dental appliance, one or more dental attachment devices 10 may be used to fix the dental appliance in the patient's mouth.

Figure 2:
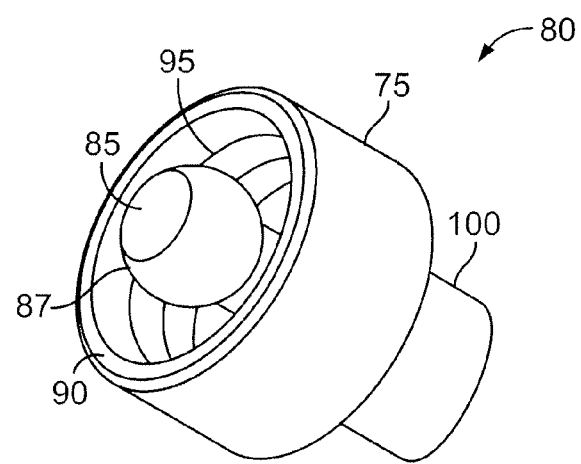
FIG. 2 is a perspective view of a cap.
Figure 3:
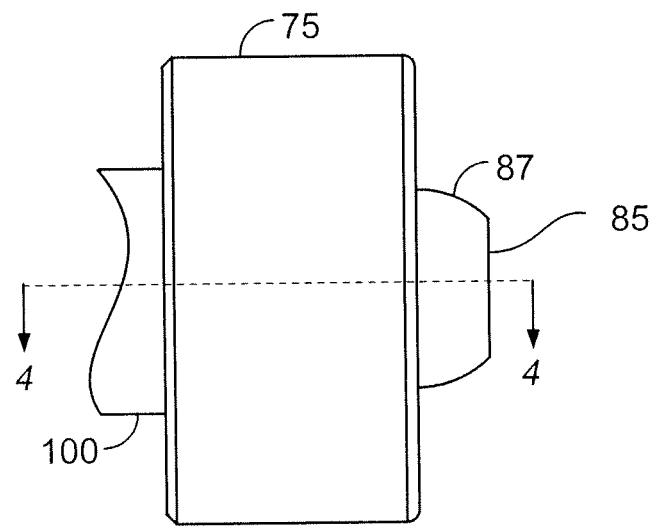
FIG. 3 is a side view of FIG. 2.
Figure 4:
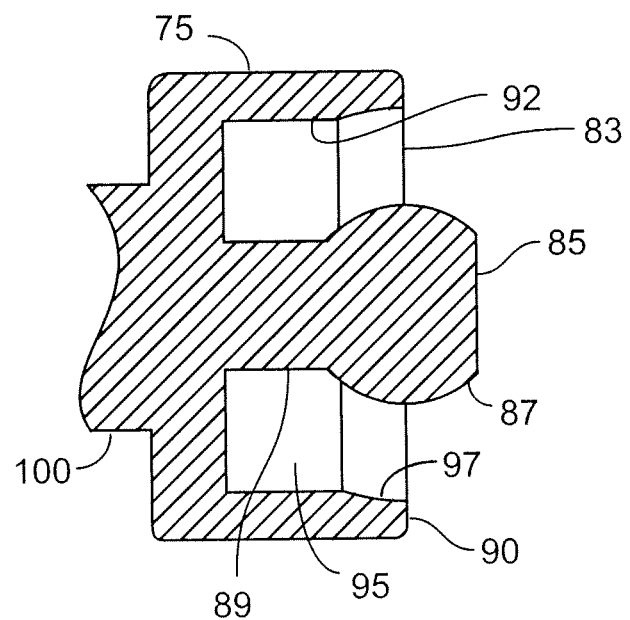
FIG. 4 is a cross-sectional view of FIG. 3.
Figure 5:
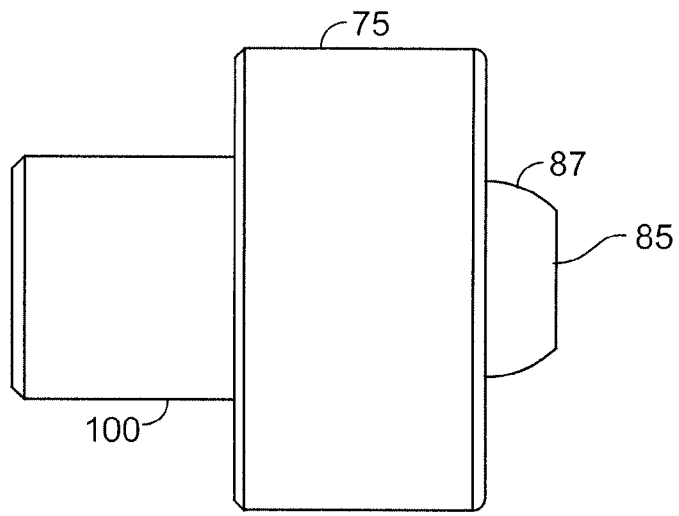
FIG. 5 is a side view of a cap having a short post attachment.
Figure 6:
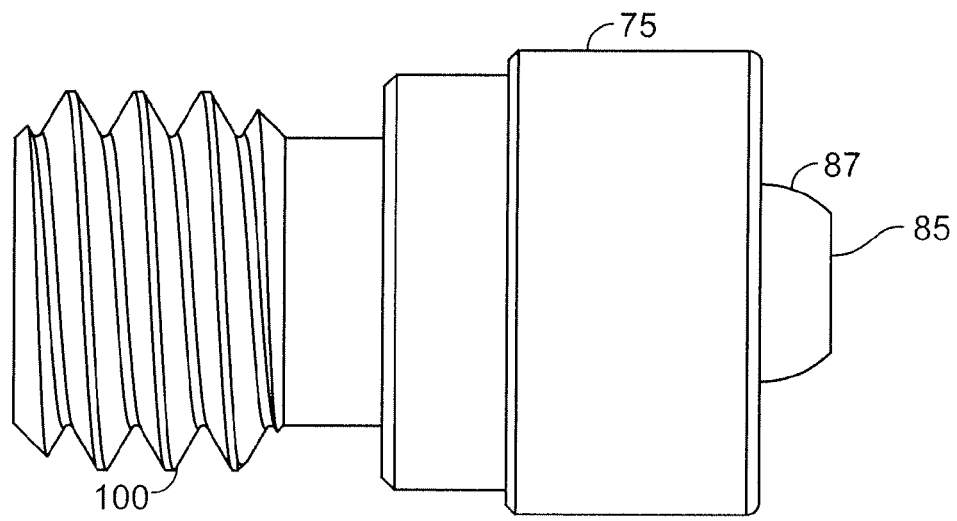
FIG. 6 is a side view of a cap having a screw attachment.
Figure 7:
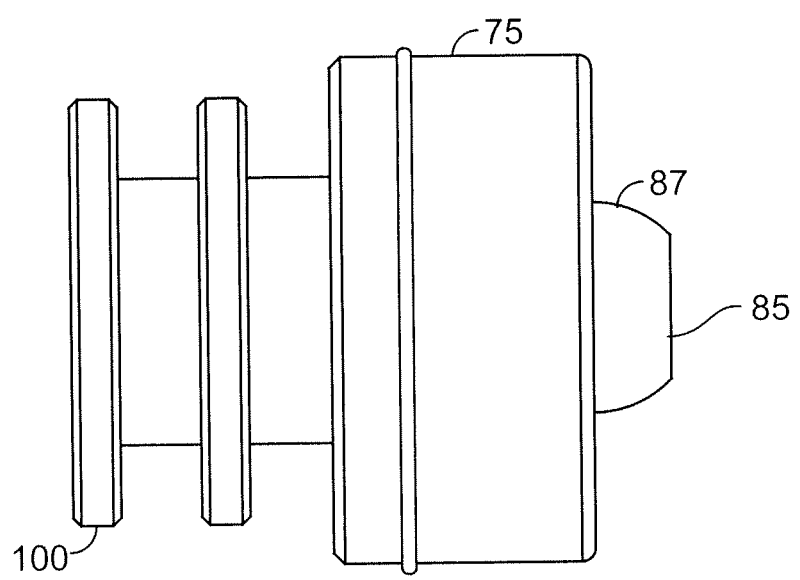
FIG. 7 is a side view of a cap having an adhesive attachment.

FIGS. 2 to 4 illustrate one embodiment of the cap 80. The cap 80 comprises an attachment portion 100 and a body portion 75, the body portion 75 having an open end 83 and an inner cavity 95 forming an annular wall 90. The body portion 75 may be any shape suitable for securing the cap 80 in a dental appliance. By way of example, FIGS. 2 to 4 represent the outer shape as generally cup-shaped or cylindrical; however, other shapes known in the art may be employed. The inner cavity 95 has an inner annular surface 92 with a distal end portion having a concave lip 97. The concave lip 97 is designed to correspond with the outer convex surface 35 of the abutment 20. The annular wall 90 surrounds a retention head 85 comprising a head portion 87 and a shaft 89. The head portion 87 is substantially spherical or ball-shaped. In alternative embodiments, the head portion 87 may be substantially polygonal or spheroid. The head portion 87 can project above the lip of the annular wall 90. In an alternative embodiment, the head portion 87 can be level or below the lip of the annular wall 90. The attachment portion 100 is provided to secure in the dental appliance by structures or techniques well known and understood by those skilled in the art, including but not limited to, a short post (FIG. 5), a screw (FIG. 6), or an adhesive (FIG. 7). Such methods and techniques will not be repeated herein, and the figures are provided as exemplary only and not meant to limit the techniques of attaching the cap to a dental appliance.

In one embodiment, the cap 80 can be integral with the dental appliance and made of titanium, titanium alloys, cobalt-chromium-molybdenum alloys, stainless steel with a titanium nitride coating, zirconium, tantalum, gold, platinum, palladium, hafnium and tungsten, as well as other materials known to those of skill in the art. Both the attachment portion 100 and body portion 75 may be recessed in the dental appliance. In another embodiment, the body portion 75 may be partially recessed in the dental appliance. In still another embodiment, only the attachment portion 100 may be recessed in the dental appliance.

In one embodiment of the cap 20, the head portion 87 has a diameter in the range of about 0.05 in to about 0.15 in. Illustratively, the diameter of the head portion 87 is about 0.05 in, about 0.06 in, about 0.07 in, about 0.08 in, about 0.09 in, about 0.10 in, about 0.11 in, about 0.12 in, about 0.13 in, about 0.14 in, and about 0.15 in.

Figure 8:
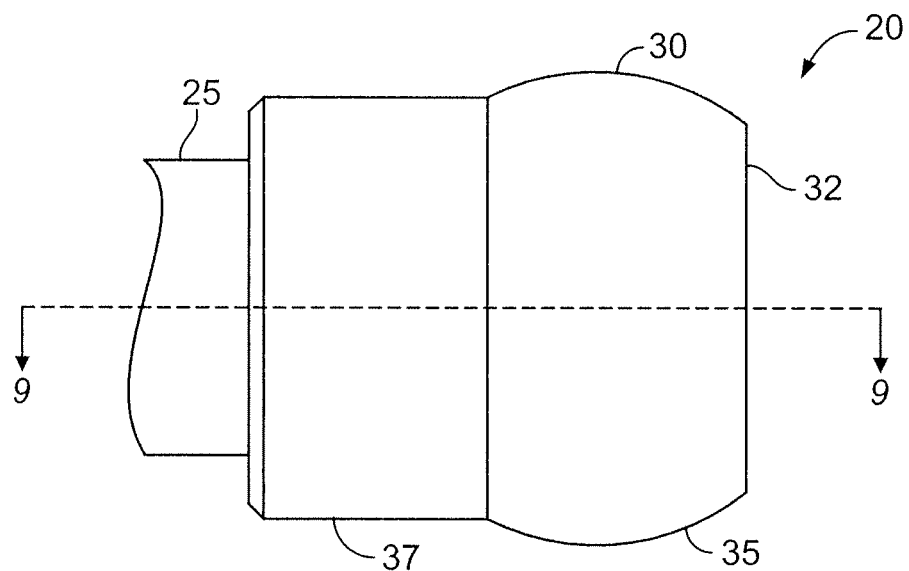
FIG. 8 is a side view of an abutment.
Figure 9:
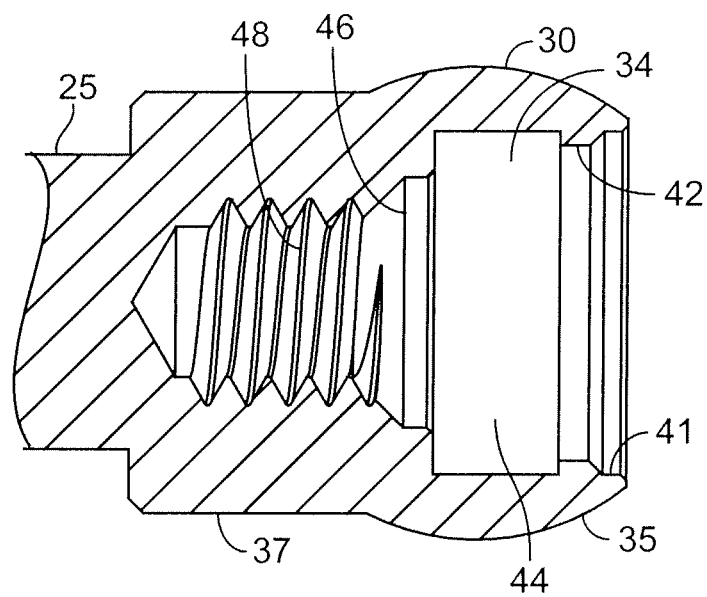
FIG. 9 is a cross-sectional view of FIG. 8.

FIGS. 8 and 9 illustrate one embodiment of the abutment 20. The abutment comprises an upper portion 30 having an open end 32 and a socket 34 for receiving the ring 50 and the retention head 85 of the cap 80, a cuff portion 37, and an attachment portion 25 for attachment to a non-vital tooth root or implant. The upper portion 30 has a convex outer surface 35 extending from the open end 32 to the cuff portion 37. The cuff portion 37 may be of different heights to accommodate patients with different tissue heights. The socket 34 extends from the open end 32 through part or all of the length of the upper portion 30 and/or cuff portion 37, and is designed to accommodate the ring 50 and the retention head 85 of the cap. The socket 34 has an annular lip 41, an annular ring 42, a cylindrical cavity 44, and a hemispherical or bowl-shaped portion 46. The socket 34 receives the ring 50 by snap-engagement over the annular ring 42 of the abutment 20, which fits into the corresponding annular groove 60 of the ring 50. The head portion 87 of the retention head 85 snap-fits through the ring 50 and is positioned in the hemispherical portion 46, securing the cap onto the abutment. A tool-receiving bore 48 extends inwardly from the bottom of the socket 34 and can be threaded and/or polygonal, for example, hexagonal with flat faces, for engagement by a suitable tool for attaching the abutment 20 to a non-vital tooth root or implant. The attachment portion 25 can be adapted to be compatible with commercially available implants, or configured as a tooth root abutment, mini-implant, or an intermediary abutment as discussed below.

The abutment 20 described herein can be made of suitably strong material such as titanium, titanium alloys, cobalt-chromium-molybdenum alloys, stainless steel with a titanium nitride coating, zirconium, tantalum, gold, platinum, palladium, hafnium and tungsten, as well as other materials known to those of skill in the art. The abutment 20 can be made in a range of different sizes to fit a number of different implants, tooth roots, or intermediary abutment. The length of the abutment 20 is in the range of about 1 mm to about 10 mm. In further embodiments, the length can be about 1 mm, about 2 mm, about 3 mm, about 4 mm, about 5 mm, about 6 mm, about 7 mm, about 8 mm, about 9 mm, and about 10 mm.

Figure 10:
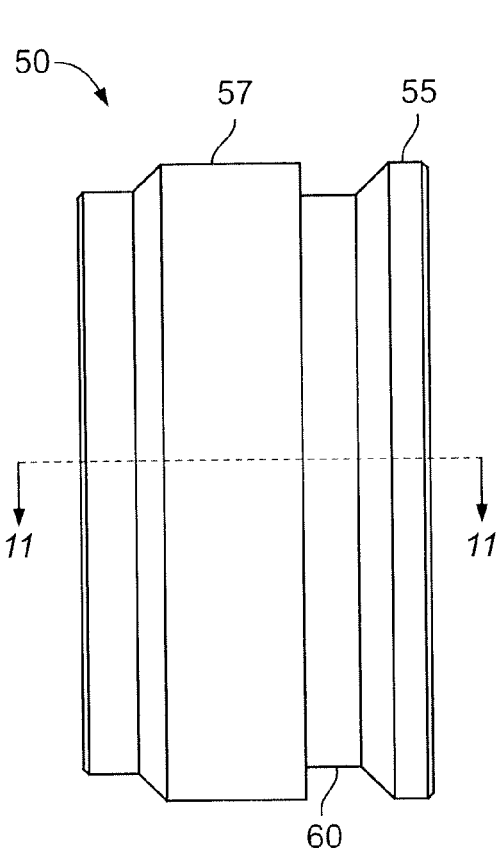
FIG. 10 is a side view of a ring.
Figure 11:
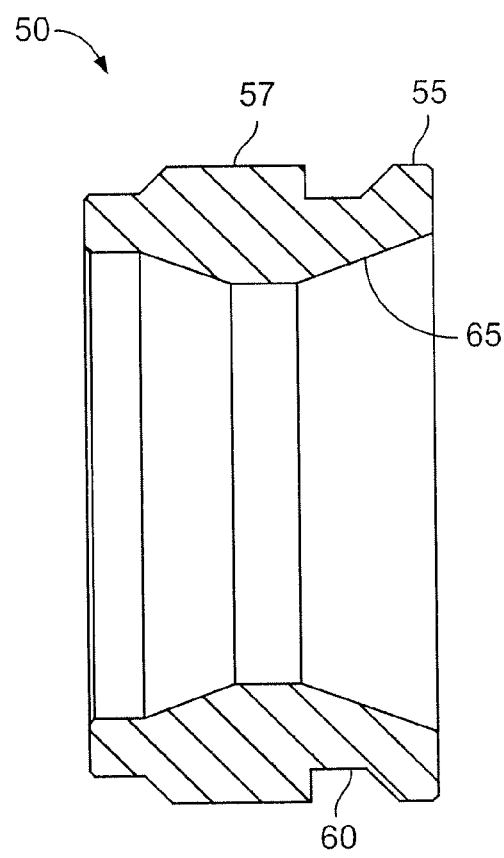
FIG. 11 is a cross-sectional view of FIG. 10.

The ring 50, shown in FIGS. 10 and 11, is adapted for engagement in the socket 34 of the abutment 20 for retention of cap 80, which is integral with the dental appliance. Referring to FIG. 10, the ring 50 has two annular flanges 55 and 57 separated by an annular seat or groove 60 to snap-fit engaged the corresponding annular ring 42 in the socket 34 of the abutment 80. The current embodiment should not limit the type of snap-fit engagement contemplated herein as other forms of snap-fit engagement are known in the art. For example, one or more annular flanges can be used to snap-fit engage the ring 50, as well as other forms for snap-fit engagement. The inner surface 65 of the ring 50, as shown in FIG. 11, is inwardly tapered from both the top and bottom, forming an hour-glass shape. The ring 50 can be made of suitably durable and flexible material such as nylon, PEEK, delrin, and other polymers known in the art, and metals such as titanium, stainless steel, etc., as well as other materials known to those of skill in the art.

Figure 12:
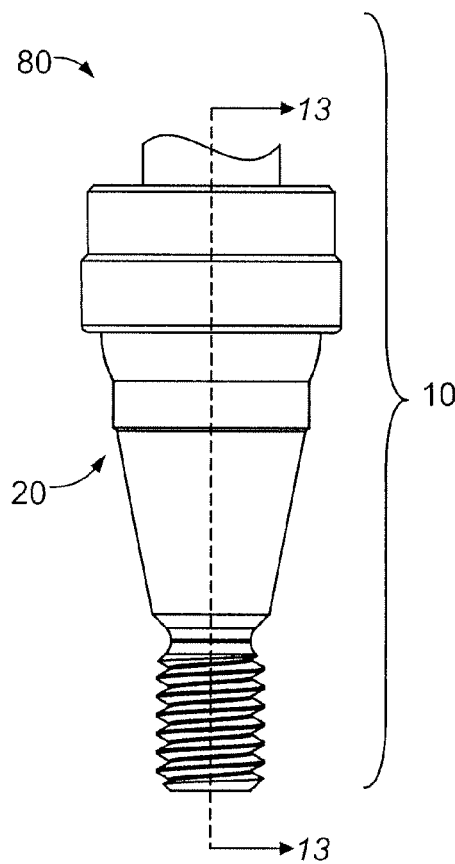
FIG. 12 is a side view of the assembled dental attachment device of FIG. 1.
Figure 13:
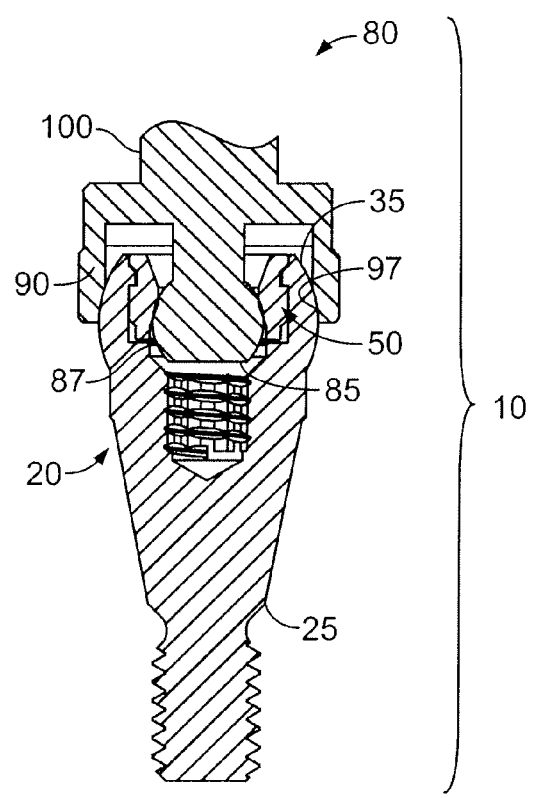
FIG. 13 is a cross-sectional view of FIG. 12.

FIGS. 12 and 13 illustrate one embodiment of the assembled dental attachment device for securing a dental appliance in the mouth of a patient. To assemble the dental attachment device, the ring 50 is snap fit over the annular ring 42 into the socket 34. The cap 80 (which can be integral with a dental appliance) is positioned over the abutment, and the retention head 85 is engaged into the socket 34 and snap fit through the ring 50. The head portion 87, or a portion thereof, is received into the hemispherical or bowl-shaped portion 46. The snap-fit engagement of the head portion 87 of the retention head 85 and ring 50 secures the cap onto the abutment. At the same time, the annular wall 90, in particular the concave lip 97, is engaged over the convex outer surface 35 of the abutment 20. The frictional forces, as well as the angle of convergence, between the two corresponding surfaces 97 and 35 also secures the cap to the abutment, while at the same time allow for a range of divergence between the cap 80 relative to the abutment 20. The tightened fit between the cap 80 and abutment 20 helps to seal the device from oral fluids in an effort to prevent microbial contamination and plaque traps.

Figure 14:
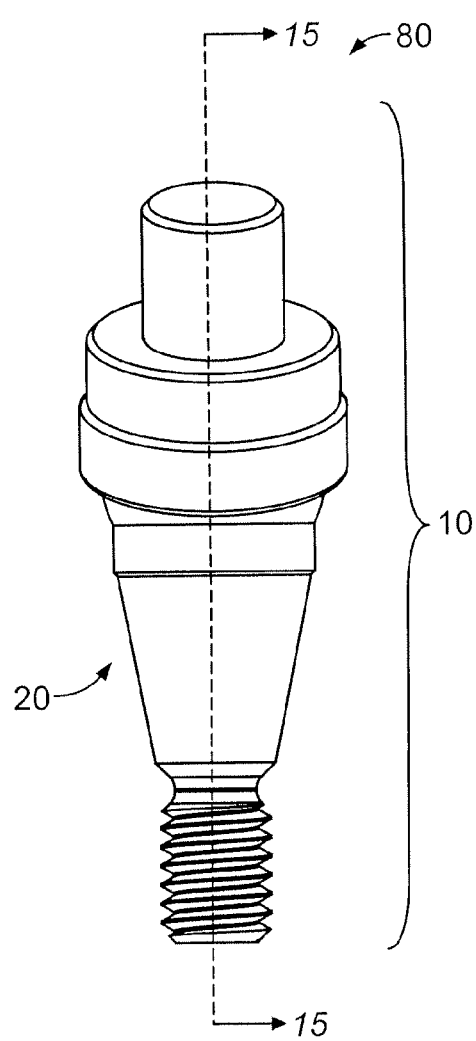
FIG. 14 is a side view of the assembled dental attachment device of FIG. 1 with a divergence between the cap and abutment.
Figure 15:
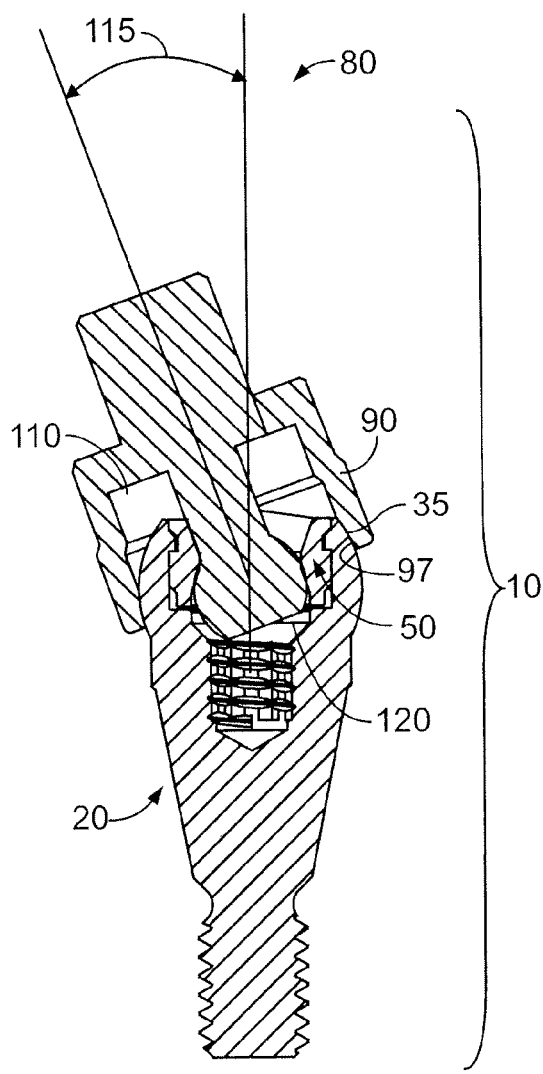
FIG. 15 is a cross-sectional view of FIG. 14.

Referring to FIGS. 14 and 15, when the dental attachment device 10 is assembled, there is a gap 110 between the cap 80 and the abutment 20 and a gap 120 between the ball-type head portion 87 and the hemispherical or bowl-shaped portion 46, which allows the cap 20 to diverge or pivot or swivel relative to the abutment 20. The range of divergence 115 between the cap 80 and abutment 20 is 0° to about 20°. Illustratively, the cap diverges relative to the abutment at an angle of 0°, about 1°, about 2°, about 3°, about 4°, about 5°, about 6°, about 7°, about 8°, about 9°, about 10°, about 11°, about 12°, about 13°, about 14°, about 15°, about 16°, about 17°, about 18°, about 19°, and about 20°. The divergence of the cap 80 relative to the abutment 20 is shown as reference numerical 115. However, even at the range of divergence, the annular wall 90 (and concave lip 97) maintains contact with the outer surface 35 of the abutment 20 to ensure frictional contact and help to create a seal between the cap 80 and abutment 20.

Figure 16:
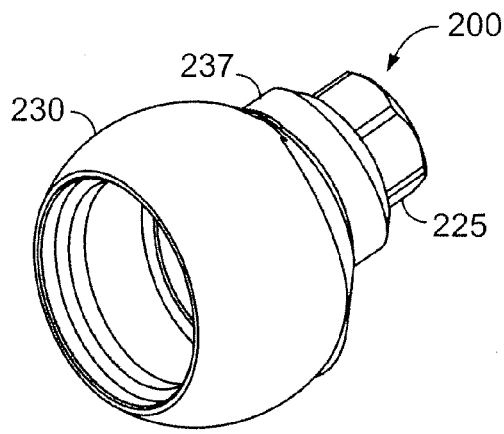
FIG. 16 is a perspective view of 20° pre-angled abutment.
Figure 17:
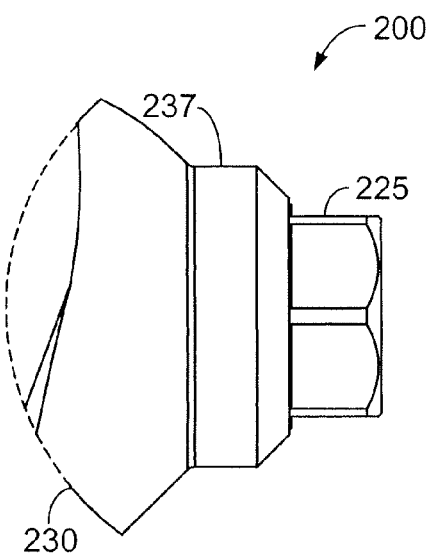
FIG. 17 is a side view of FIG. 16.
Figure 18:
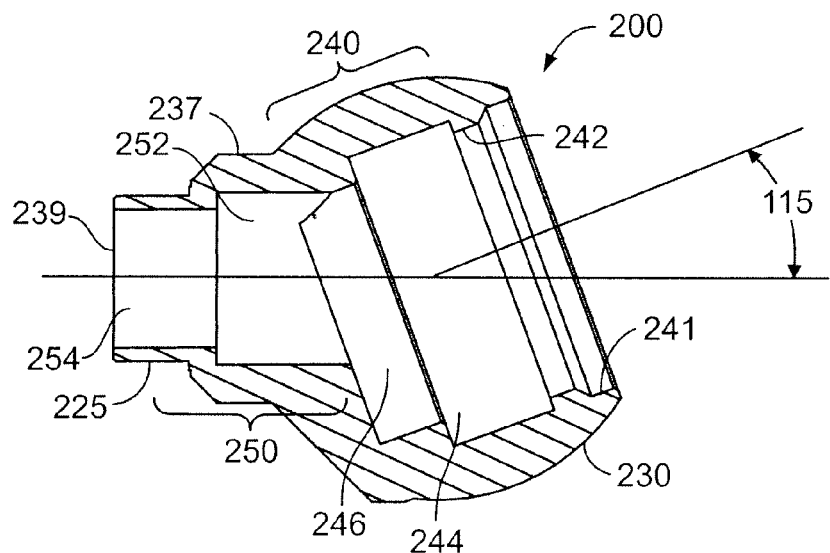
FIG. 18 is a cross-sectional view of FIG. 17.

FIGS. 16 to 18 illustrate one embodiment of a pre-angled abutment 200. The pre-angled abutment 200 is similar to that of the previous embodiment described in FIGS. 8 and 9. Referring to FIGS. 16 to 18, the pre-angled abutment 200 comprises an upper portion 230, a cuff portion 237, an attachment portion 225, and a through bore 239. The through bore 239 comprises a first portion 240 and a second portion 250. The first portion 240 is similar to socket 34 of FIG. 9, having an annular lip 241, annular ring 242, a cylindrical cavity 244, and a lower portion 246. The socket 234 receives the ring 50 by snap-engagement over the annular ring 42 of abutment 20, which fits into the corresponding annular groove 60 of the ring 50. The head portion 87 of the retention head 85 snap-fits through the ring 50 and is positioned in the lower portion 246. The second portion 250 comprises a first cylindrical portion 252, that accepts a retaining screw to fasten the pre-angled abutment to an implant, and a second cylindrical portion 254, the second cylindrical portion 254 having a smaller diameter than the first cylindrical portion 252.

In one embodiment, the upper portion 230 is at an angled of 20° from a central axis of the cuff 237 and attachment 225 portions as shown in FIG. 18. The pre-angled abutment is exemplary and not limiting as the pre-angled abutment can be at an angle of, about 10°, about 15, about 20°, and about 25°. In additional embodiments, the pre-angle abutment can be at an angle between about 5° to about 45°, about 10° to about 40°, about 15° to about 35°, and about 20° to about 30°. By way of example, the 20° pre-angled abutment, together with the range of divergence, allows a divergence up to about 40° of the cap 80 relative to the central axis of the cuff 237 and attachment 225 portions of the abutment 20. Illustratively, the range of divergence of the cap 20 is about 20°, about 21°, about 22°, about 23°, about 24°, about 25°, about 26°, about 27°, about 28°, about 29°, about 30°, about 31°, about 32°, about 33°, about 34°, about 35°, about 36°, about 37°, about 38°, about 39°, and about 400° relative to the 20° pre-angled abutment 200.

Referring to FIGS. 19 and 20, the pre-angled abutment 200 can be secured in an implant 233 by means of the attachment portion 225, which is secured in an implant using a retaining screw 260. The implant 233 comprises a first end cuff portion 232 having an open end comprising a cavity 238 for receiving the attachment portion 225 of the pre-angled abutment 200 and a threaded bore 236, and a second end thread shaft 243. The cavity 238 is designed in size and shape to mate with the attachment portion 225 of abutment 200. For assembly, the attachment portion 225 of the pre-angled abutment 200 is fitted into the cavity 238 of the implant 233. The retaining screw 260 is set through the through bore 239 and screwed into the threaded bore 236, thereby securing the pre-angled abutment 200 to the implant 230.

Figure 21:
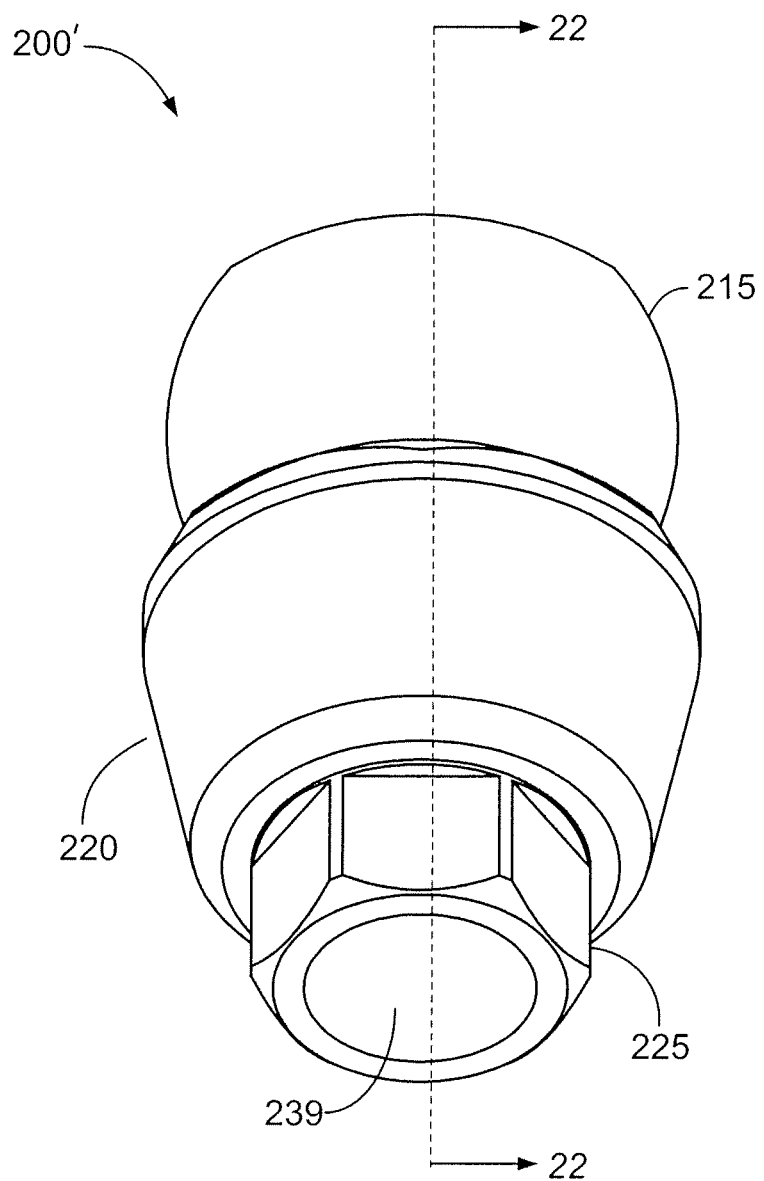
FIG. 21 is an alternative embodiment of a 20° pre-angled abutment.
Figure 22:
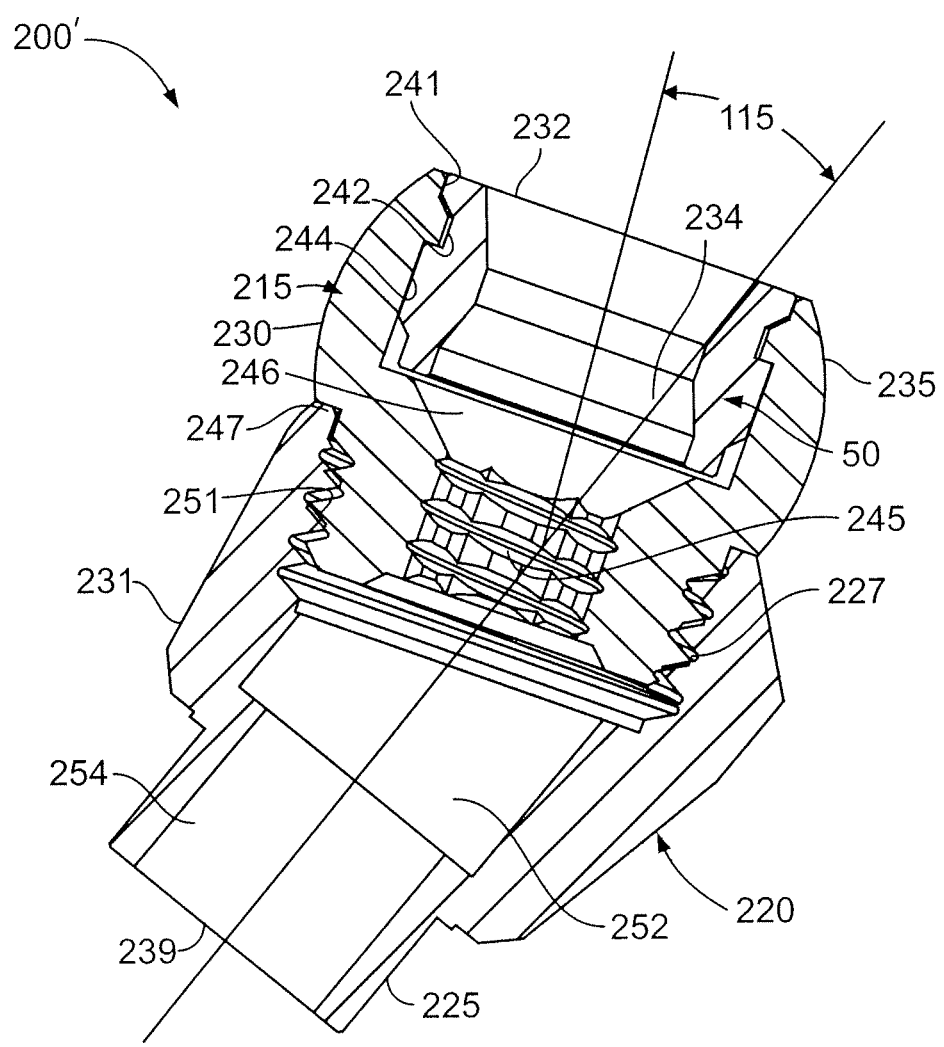
FIG. 22 is a cross-sectional view of FIG. 21.

An alternative embodiment of a two-piece pre-angled abutment 200' is illustrated in FIGS. 21 and 22. The pre-angled abutment 200' is similar to that of the previous embodiment described in FIGS. 16 to 18, and like reference numbers will be used for like parts. The pre-angled abutment 200' comprises a first component 215 having an upper portion 230 and a threaded shaft 227, and a second component 220 having a body portion 231, an attachment portion 225, and through bore 239. The upper portion 230 has an open end 232 and a socket 234 for receiving the ring 50 and the retention head 85 of the cap 80, and a convex outer surface 235 extending from an open end 232 to the threaded shaft 227. The socket 234 has an annular lip 241, annular ring 242, a cylindrical cavity 244, and a lower portion 246. A tool-receiving bore 245 extends inwardly from the bottom of the socket 234. The body portion 231 has a open end 247 and a cavity having a thread portion 251, a first cylindrical portion 252, and a second cylindrical portion 254 having a smaller diameter than the first cylindrical portion 252.

The thread portion 251 is at a predetermined angled 115 from a central axis of the first and second cylindrical portions 252 and 254, respectively, and in turn, when assembled, the first component 215 will be at the same predetermine angle. For example, the pre-angled abutment can be at an angle of about 10°, about 15, about 20°, and about 25°. In additional embodiments, the pre-angle abutment can be at an angle between about 5° to about 45°, about 10° to about 40°, about 15° to about 35°, and about 20° to about 30°. By way of example, the 20° pre-angled abutment, together with the range of divergence, allows a divergence up to about 40° of the cap 80 relative to the first and second cylindrical portions 252 and 254, respectively, of the abutment 200'. Illustratively, the range of divergence of the cap 20 is about 20°, about 21°, about 22°, about 23°, about 24°, about 25°, about 26°, about 27°, about 28°, about 29°, about 30°, about 31°, about 32°, about 33°, about 34°, about 35°, about 36°, about 37°, about 38°, about 39°, and about 40° relative to the 20° pre-angled abutment 200'.

Figure 23:
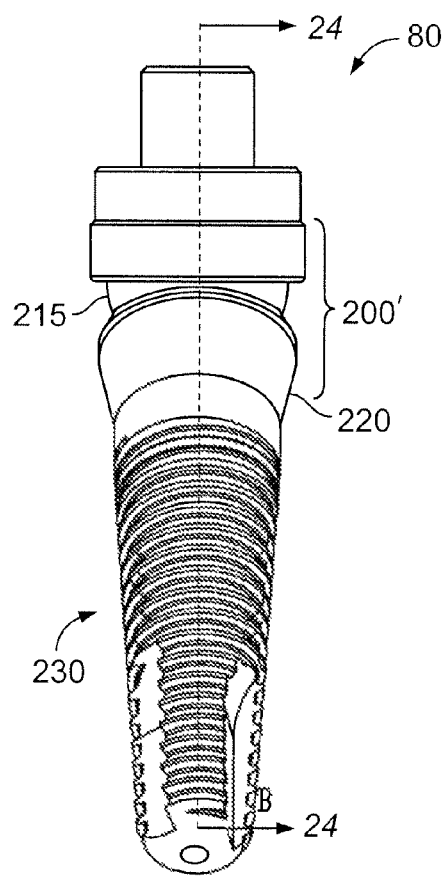
FIG. 23 is a side view of the assembled dental attachment device with a 20° pre-angled abutment of FIG. 21
Figure 24:
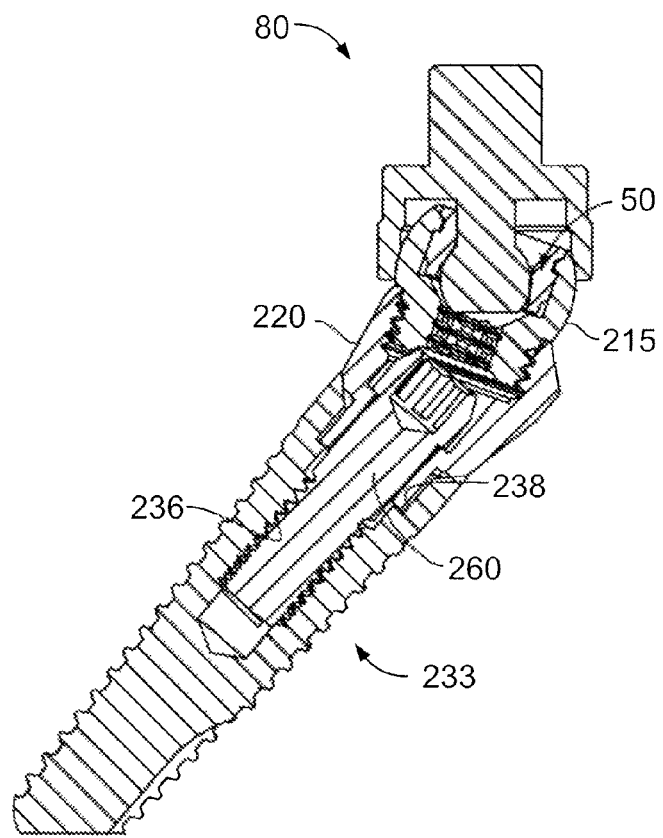
FIG. 24 is a cross-sectional view of FIG. 23.

The two-piece pre-angled abutment 200', as shown in FIGS. 23 and 24, can be assembled and secured in an implant 233 using a retaining screw 260 as shown in FIG. 24. The attachment portion 225 of the second component 220 is fitted into cavity 238 of the implant 233. The retaining screw 260 is set through the through bore 239 and screwed into the threaded bore 236, thereby securing the second component 220 to the implant 230. The threaded shaft 227 of the first component 215 is engaged and secured into the threaded portion 251 of the cavity 236 of the second component 220.

In another embodiment, the dental attachment device 10 comprises a cap 80 for securing the dental appliance (not shown) and an abutment 20 for attachment to a non-vital tooth root, implant or the like. The cap 80 is positioned over and engaged with abutment 20 providing a metal-to-metal engagement of the inner annular surface 92 (and concave lip 97) of wall 90 over the convex outer surface 35 of the abutment 20. The mating of these two surfaces results in a galling or press fit effect that creates retentive force between the components and secures the cap 80 to the abutment 20. The metal-to-metal interference and resulting retention is achieved by the compressive biting force applied at the time of seating the prosthesis and caps on the abutments and then further through the continuous mastication forces imparted by the patient.

Figures 25, 26:
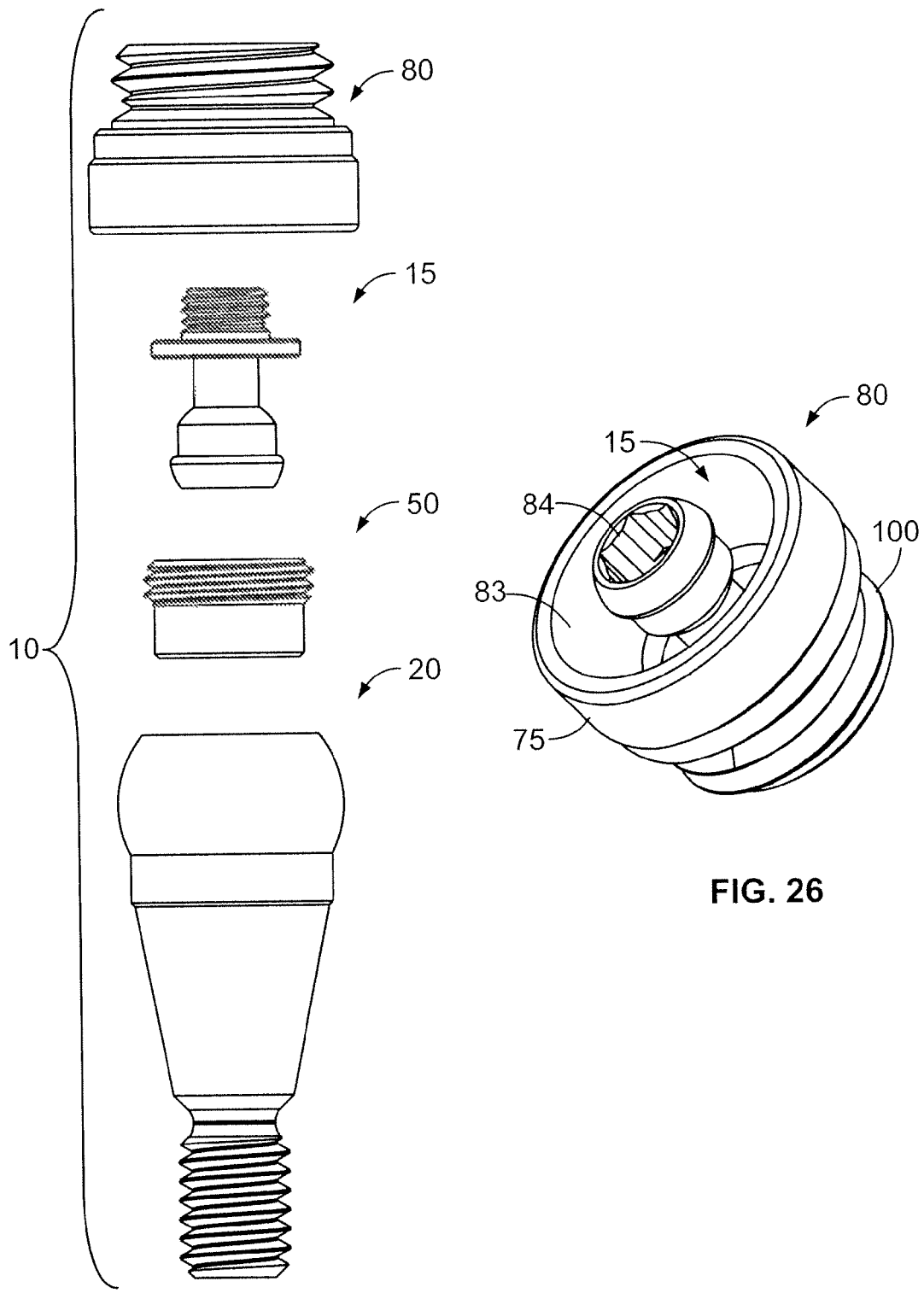
FIG. 25 is an exploded view of an alternative embodiment of a dental attachment device.
FIG. 26 is a perspective view of an alternative embodiment of a cap.

Referring to FIG. 25, another embodiment of the dental attachment device for securing a dental appliance is illustrated. Dental attachment device 10 comprises a cap 80 for securing the dental appliance (not shown), an abutment 20 for attachment to a non-vital tooth root, implant or the like, removable ball 15, and a retainer ring 50. The cap 80 engages with the abutment 20, removable ball 15 and ring 50 as indicated by the dotted center line of FIG. 25 to secure a dental appliance in the mouth of a subject. The abutment 20 may be adapted to be compatible with commercially available implants, such as the Astra implant (Astra Tech Inc., Waltham, Mass.), Brånemark implant (Nobel Biocare, Zurich, Switzerland), and the Straumann implants (Straumann USA LLC, Andover, Mass.), or configured as a tooth root abutment, mini-implant, or in a configuration that can be adapted to an intermediary abutment, which would be secured to a dental implant. Abutment 20 further comprises a cuff portion 37 to indicate the approximate position of the patient's gum line against abutment 20 when inserted. Cap 80 may be designed to integrate in or connect to a dental appliance by, for example but not limited to, a post, a screw, or an adhesive such as acrylic, bisacrylic, or other suitable cements. In this embodiment (FIG. 25), cap 80 has threads for attachment into, for example, a CAD/CAM fabricated metal bar.

Figure 27:
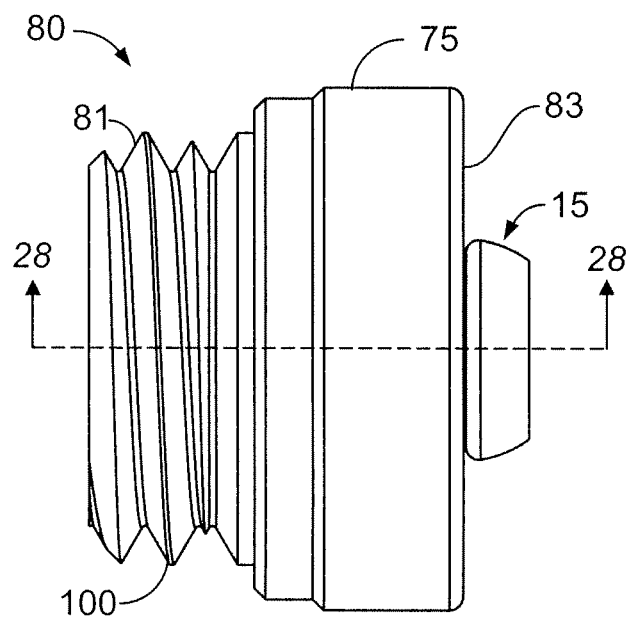
FIG. 27 is a side view of FIG. 26.
Figure 28:
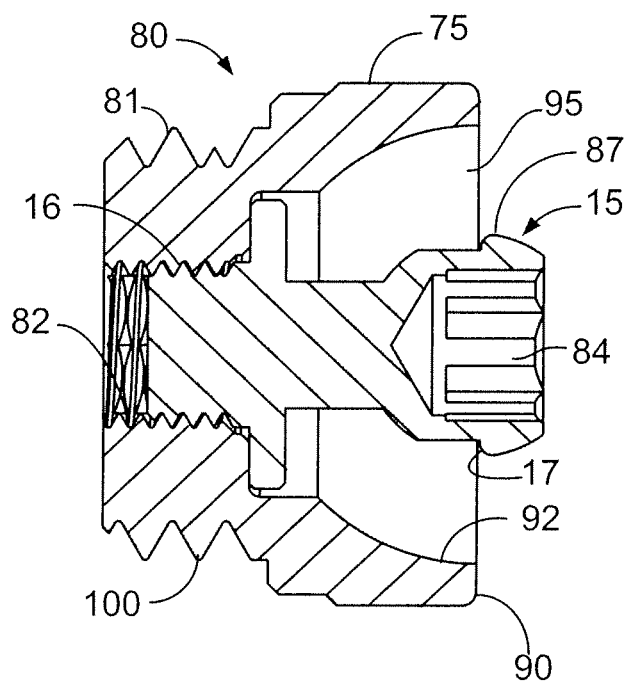
FIG. 28 is a cross-sectional view of FIG. 27.

FIGS. 26 to 28 illustrate one embodiment of the cap 80 with removable ball 15. The cap 80 comprises an attachment portion 100 and a body portion 75 having an inner cavity 95 forming an annular wall 90. While shown as circular in shape, body portion 75 may take any shape suitable for securing the cap 80 in a dental appliance. Removable ball 15 comprises driving feature 84, in this case, but not limited to, an internal hex for engagement of a wrench to seat and torque the removable ball in the cap 80 by the dental clinician. FIG. 27 illustrates a side view of cap 80 and removable ball 15, in this case the CAD/CAM cap. As shown in FIG. 28, the inner cavity 95 in open end 83 has an inner annular, concave surface 92. The concave surface 92 is designed to correspond to and engage over the outer convex surface 35 of the abutment 20. The annular wall 90 surrounds removable ball 15, with a head portion 87 that is substantially spherical or ball-shaped. In alternative embodiments, removable ball 15 may be other suitable shapes such as polygonal or spheroid. In alternative embodiments, removable ball 15 or driving feature 84 or both may project above, below, or at level with the lip of annular wall 90.

Attachment portion 100 is provided to secure the dental appliance by structures or techniques well-known and understood by skilled artisans, including but not limited to, a short post, a screw, or an adhesive. Such techniques will not be repeated herein, and the figures are provided as exemplary only and not meant to limit the present invention.

Referring to FIG. 27, cap 80 comprises external threads 81, which engage corresponding threads of a dental appliance. Cap 80, as shown in FIG. 28, further comprises internal threads 82, which engage corresponding external threads 16 on removable ball 15. Removable ball 15 comprises edge 17 to increase the retention of removable ball 15 when engaged with abutment 20.

Figure 29C:
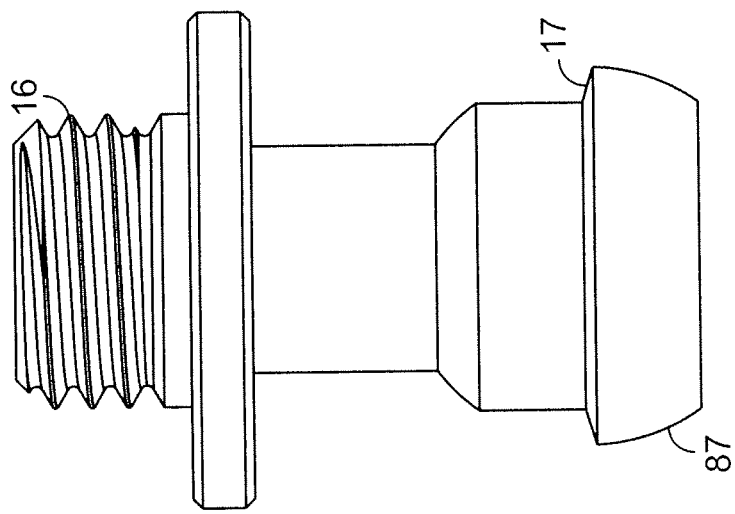
FIG. 29C is a side view of different configurations of a removable ball with high retention force.
Figure 29B:
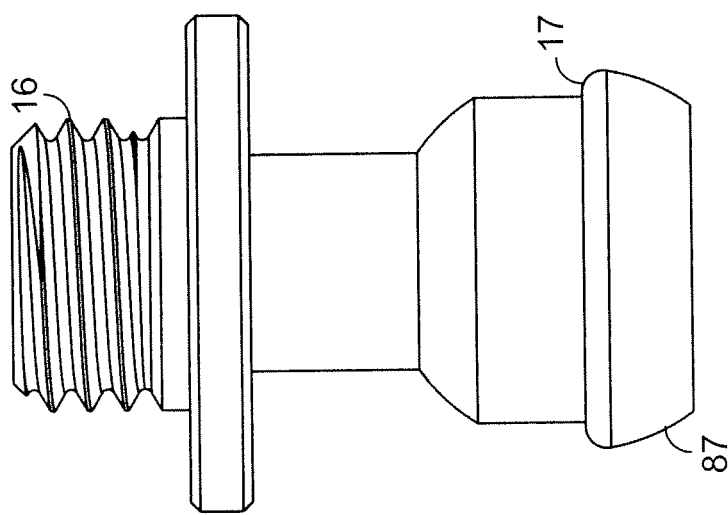
FIG. 29B is a side view of different configurations of a removable ball with medium retention force.
Figure 29A:
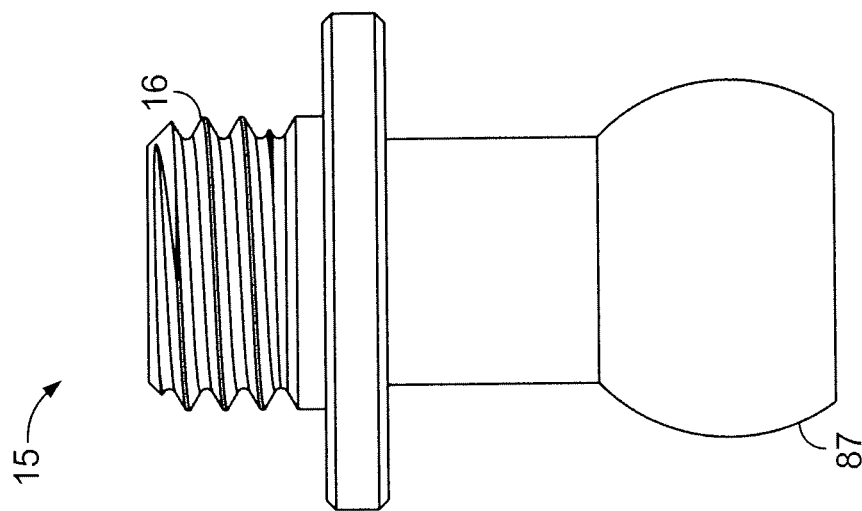
FIG. 29A is a side view of different configurations of a removable ball with low retention force.

FIGS. 29A-C illustrate three example configurations of removable ball 15, which are interchangeable by the dental professional. In FIG. 29A, head portion 87 is ball-shaped providing a retention force sufficient to prevent detachment by the patient, but less the other two configurations. Head portion 87 in FIG. 29A may be constructed of plastic and/or having a smooth, spherical surface when the ball engages with ring 50 in abutment 20.

FIG. 29B is an example of ball 15 with a head portion 87 of medium retentive force. This is achieved by making portion 87 or the entire ball 15 out of metal or other hard material. Ball 15 may also have annular lip or edge 17 that allows ball 15 to be smoothly inserted into ring 50 but seats or "bites" when removed thereby increasing the retention force.

A third configuration is illustrated in FIG. 29C of a ball 15 having a head portion 87 with a high retention force. This is created by sharpening annular flange or edge 17 so that the amount of force to remove it through retaining ring 50 and abutment 20 is increased. Head portion 87 may therefore comprise a surface feature selected from the group consisting of a barb, an annular edge, a partially annular edge or a lip.

Other configurations are possible to vary the retention force within the ring 50 and to abutment 20. Such force required is dictated by a number of factors, including but not limited to, by the metal-to-metal contact of the inner diameter of the cap with the spherical surface of the abutment, by the interference between the ball diameter and the inner diameter of the ring, by tightly controlling the vertical height of full seating of the cap to control this engagement, and the sharpness of edge 17 on head portion 87 to resist a separating movement.

Figures 30, 31:
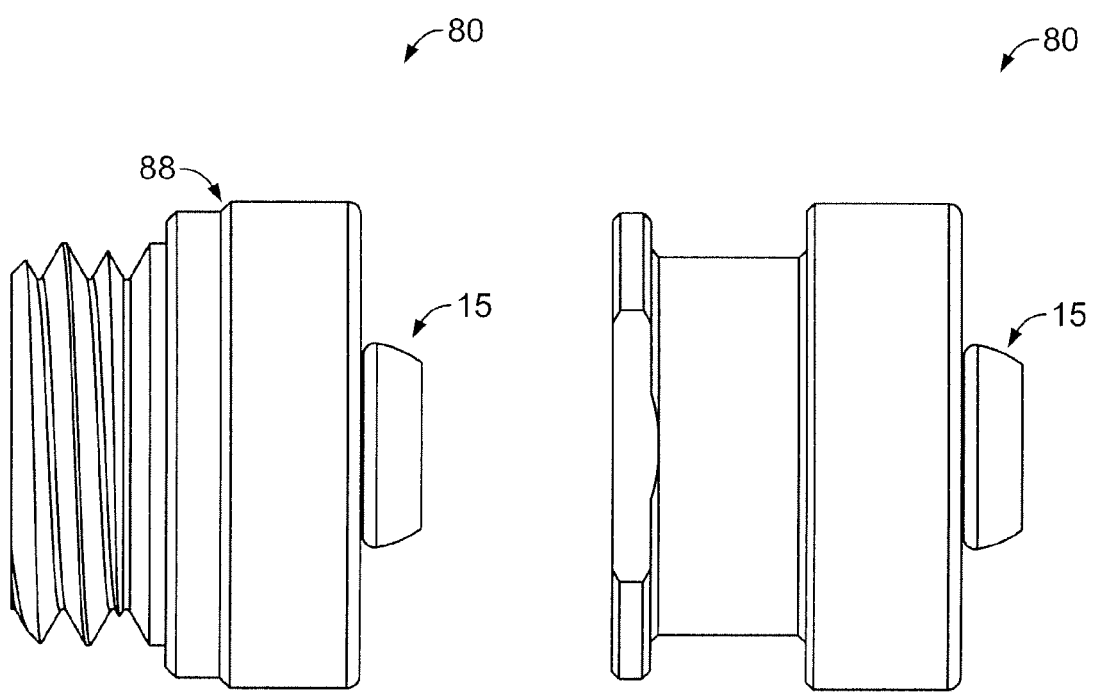
FIG. 30 is a side view of an alternative embodiment of a cap having a screw attachment.
FIG. 31 is a side view of alternative embodiment of a cap having an adhesive attachment.

FIGS. 30 and 31 illustrate two embodiments of cap 80. The cap 80 in FIG. 30 interfaces with a CAD/CAM denture bar. The arrow 88 identifies an acrylic finishing line feature where the acrylic from the surrounding denture can create a smooth finish with cap 80. This feature may be applied to any configuration of cap 80. A similar feature can be used to provide an appropriate contact point for a denture fabricated with a metal bottom. The cap 80 in FIG. 31 is for use with direct application of acrylic. Additional cap configurations may be fabricated for use with other types of denture support structures other than CAD/CAM bars or acrylic pick-up types.

Figure 32:
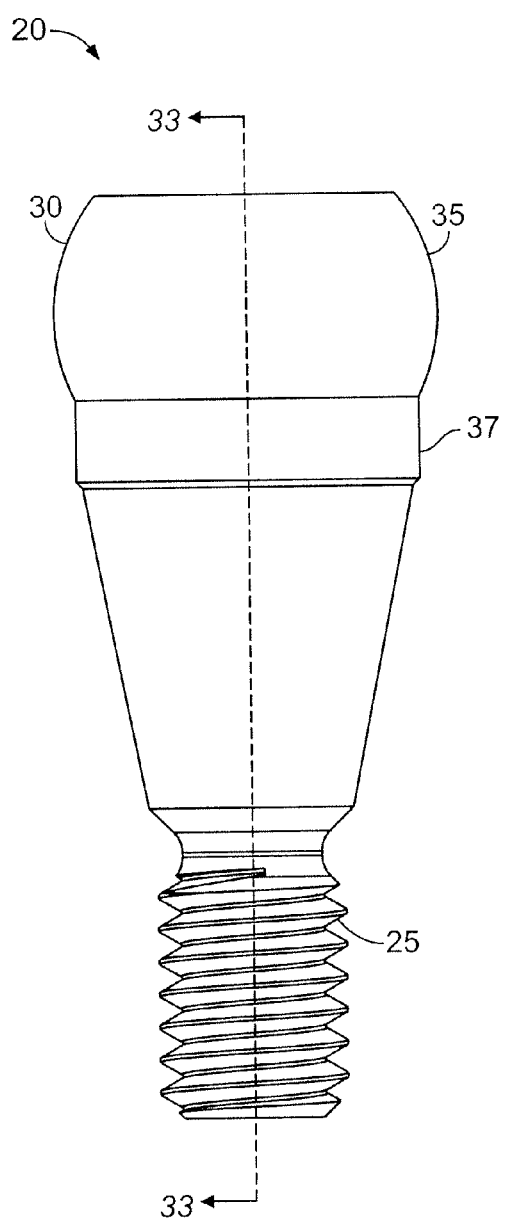
FIG. 32 is a side view of an alternative embodiment of an abutment.
Figure 33:
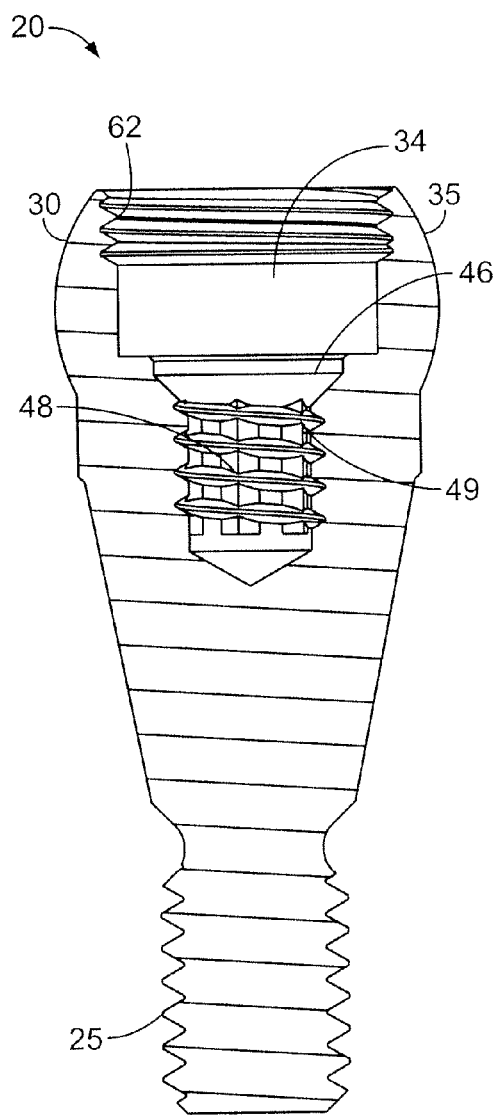
FIG. 33 is a cross-sectional view of FIG. 32.

FIGS. 32 and 33 show the abutment 20 and a cross section thereof, respectively. The abutment 20 is similar to that of the previous embodiment described in FIGS. 8 and 9, and like reference numbers will be used for like parts. The cross section of the abutment 20 shows an internal thread 49 for securing threaded components such as the healing cap 300 and the impression coping screw (not shown). There is also an internal bore 48 that acts as a driving feature for engagement by a suitable tool in order to tighten the abutment 20 into the implant. Finally, there is a socket 34 for the ring. In this case, there is a thread 62 in the abutment (the large diameter internal thread) that is used to secure the ring which is engaged by the removable balls.

Figure 34:
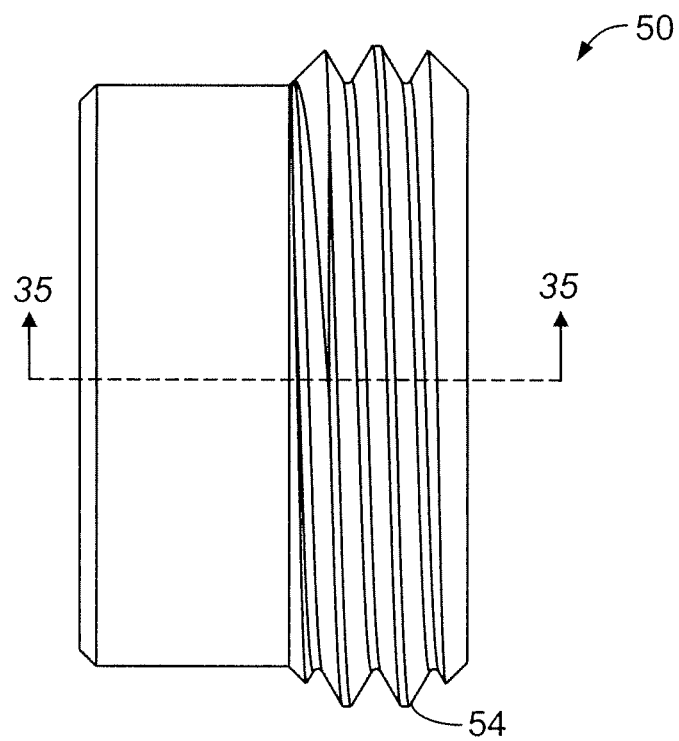
FIG. 34 is a side view of an alternative embodiment of a ring.
Figure 35:
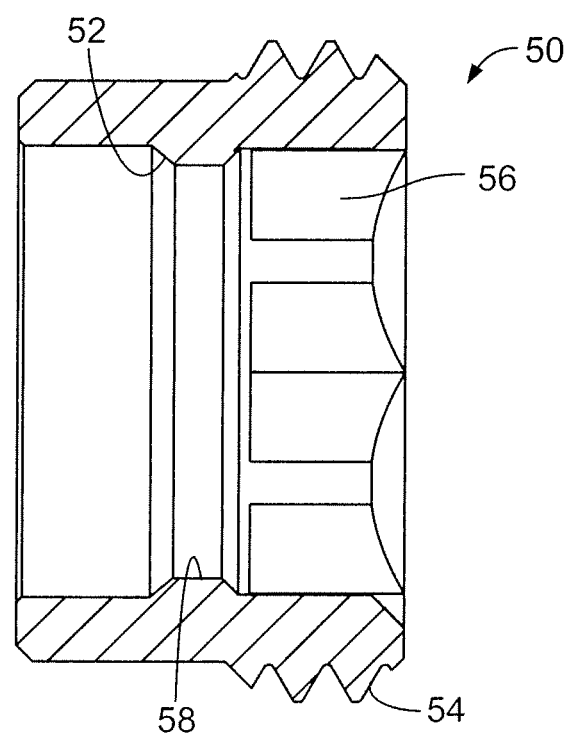
FIG. 35 is a cross-sectional view of FIG. 34

FIGS. 34 and 35 show the retention ring 50 and a cross section thereof, respectively. The side view of the ring shows the external threads 54 that, in this embodiment, are used to secure the ring 50 in the abutment 20. The ring 50 may be, and in this configuration is intended to be, removable or easily removable by the clinician, so that the ring 50 may be replaced if needed when the denture is removed, such as during routine cleaning and general restoration maintenance. The cross section of the ring shows an internal hexagon 56 which is an internal driving feature for tightening the ring into the abutment. Finally, smallest inner diameter ring or flange 58 in the ring is used to engage the removable balls 15 and generate retention. The opening 52 of that inner diameter on the left side allows for the balls to create an audible sound or "click" when fully engaged. The cap 80 and removable ball 15 interfaces with the ring (and the abutment) from right to left in FIG. 35. The ring is made out of a soft material such as plastic. In one embodiment, the ring comprises PEEK so that it has enough pliability to allow the removable balls to snap into place, but enough stiffness to maintain a sufficient amount of retention force.

Figure 36:
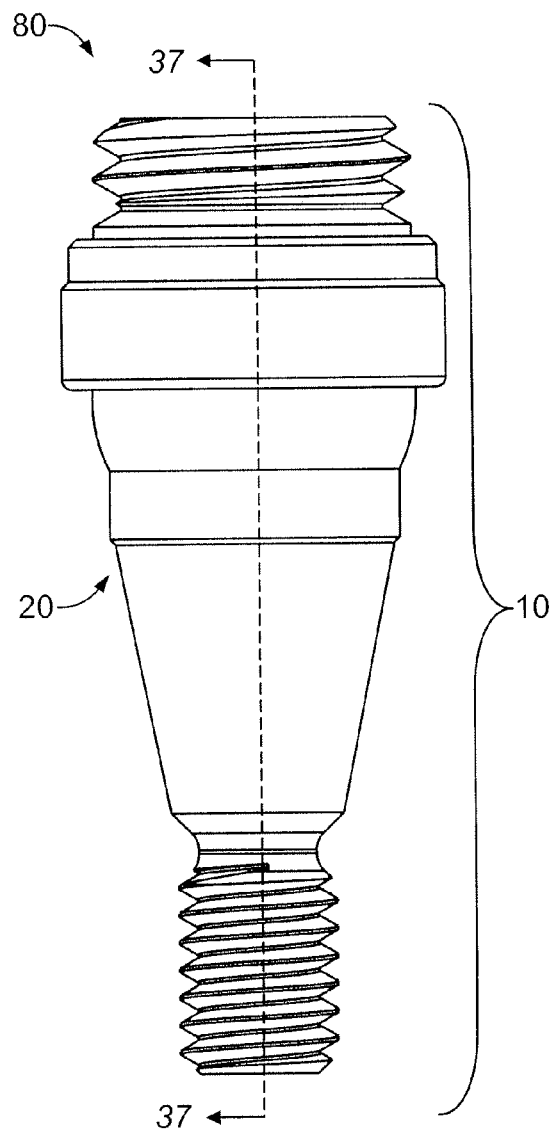
FIG. 36 is a side view of the assembled dental attachment device of FIG. 25.
Figure 37:
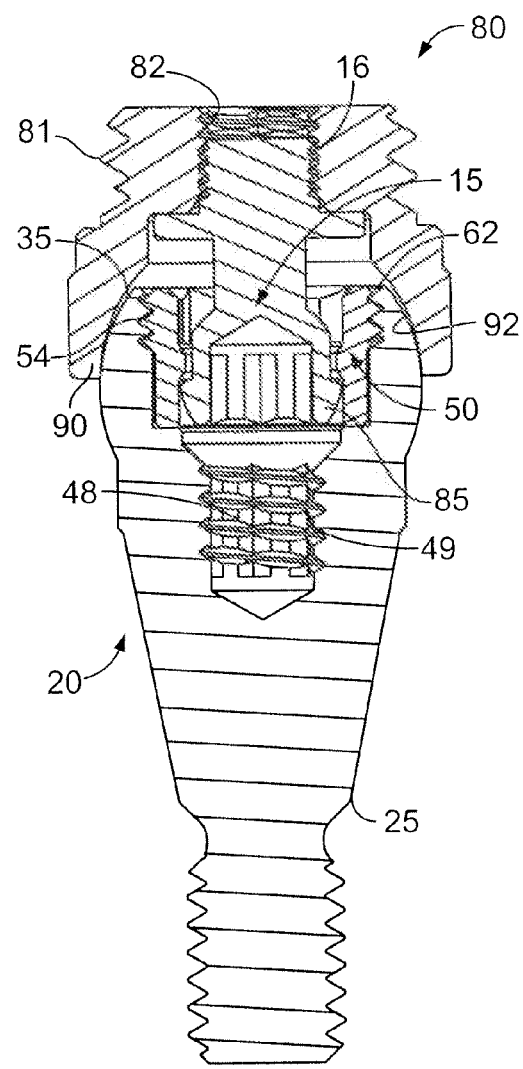
FIG. 37 is a cross-sectional view of FIG. 36.

FIGS. 36 and 37 illustrate one embodiment of the assembled dental attachment device 10 for securing a dental appliance in the mouth of a patient. To assemble the dental attachment device, the ring 50 is threadedly connected to a mating threaded portion, 54 and 62, respectively, in the socket 34. In alternative embodiments, the ring 50 may be snap-fit or press-fit engaged into the socket 34. The cap 80 (which can be integral with a dental appliance) and the removable ball 15 is positioned over the abutment, and the head portion 87 of the removable ball 15 is engaged into the socket 34 and snap fit through the ring 50. The snap-fit engagement of the head portion 87 of the removable ball 15 and ring 50 provides the retention force and secures the cap onto the abutment. Depending on the configuration of the head portion 87 (as described in FIG. 29), the retention force may be adjusted to account for variations in patients and/or clinical conditions. For example, where loading is applied to a cantilevered area of the restoration, the force of retention must be proportionally larger to ensure that the restoration does not come unseated.

An additional retention feature of the dental device 10 consists of the metal-to-metal engagement of the inner concave surface 92 of wall 90 over the convex outer surface 35 of the abutment 20. The frictional forces, as well as the angle of convergence, between the two corresponding surfaces 92 and 35 secures the cap to the abutment, while at the same time allow for a range of divergence between the cap 80 relative to the abutment 20. The tightened fit between the cap 80 and abutment 20 helps to seal the device from oral fluids in an effort to prevent microbial contamination and plaque traps.

Referring to FIGS. 38 and 39, when the dental attachment device 10 is assembled, there is a gap 110 between the cap 80 and the abutment 20 and a gap 120 between the ball-type head portion 87 and the hemispherical or bowl-shaped portion 44, which allows the cap 20 to diverge or pivot or swivel relative to the abutment 20. The range of divergence between the cap 80 and abutment 20 is 0° to about 20°. Illustratively, the cap 80 diverges relative to the abutment at an angle of 0°, about 1°, about 2°, about 3°, about 4°, about 5°, about 6°, about 7°, about 8°, about 9°, about 10°, about 11°, about 12°, about 13°, about 14°, about 15°, about 16°, about 17°, about 18°, about 19°, and about 20°. The divergence of the cap 80 relative to the abutment 20 is shown as reference numerical 115. However, even at the range of divergence, the annular wall 90 maintains contact with the outer surface 35 of the abutment 20 to ensure frictional contact and help to create a seal between the cap 80 and abutment 20.

Figure 40:
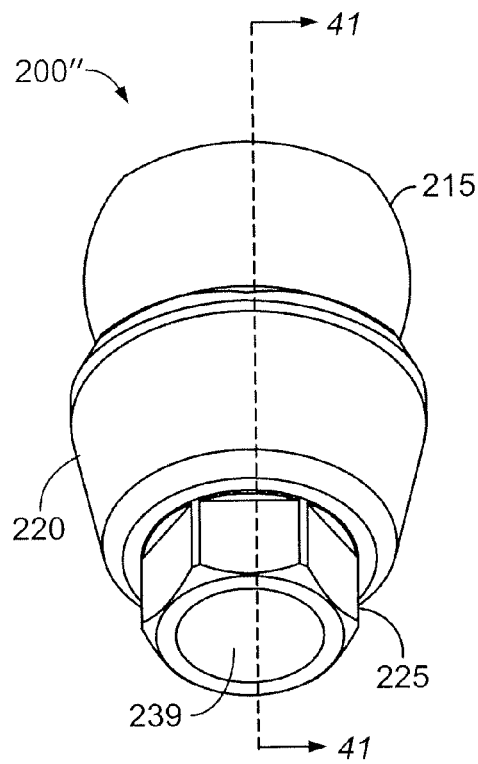
FIG. 40 is a perspective view of an alternative embodiment of a 20° pre-angled abutment.
Figure 41:
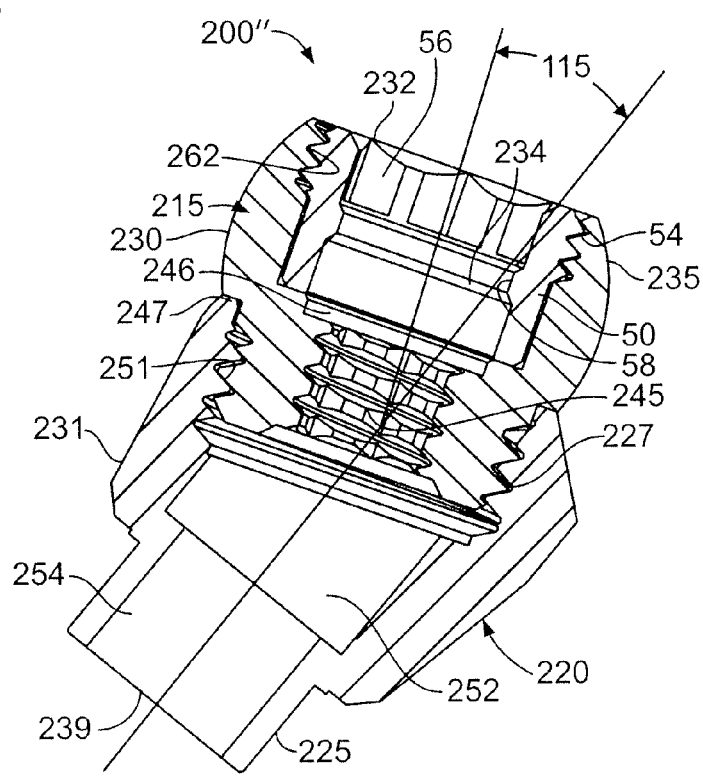
FIG. 41 is a cross-sectional side view of FIG. 40.

FIGS. 40 and 41 illustrate another embodiment of a two-piece pre-angled abutment 200". The pre-angled abutment 200" is similar to that of the previous embodiment described in FIGS. 21 and 22, and like reference numbers will be used for like parts. The pre-angled abutment 200" comprises a first component 215 having an upper portion 230 and a threaded shaft 227, and a second component 220 having a body portion 231, an attachment portion 225, and through bore 239. The upper portion 230 has an open end 232 and a socket 234 for receiving the ring 50 and the removable ball 15 of the cap 80, and a convex outer surface 235 extending from an open end 232 to the threaded shaft 227. The socket 234 has threaded portion 262, a cylindrical cavity 244, and a lower portion 246. A tool-receiving bore 245 extends inwardly from the bottom of the socket 234. The body portion 231 has a open end 247 and a cavity having a thread portion 251, a first cylindrical portion 252, and a second cylindrical portion 254 having a smaller diameter than the first cylindrical portion 252.

The thread portion 251 is at a predetermined angled 115 from a central axis of the first and second cylindrical portions 252 and 254, respectively, and in turn, when assembled, the first component will be at the same predetermine angle. For example, the pre-angled abutment can be at an angle of, about 10°, about 15, about 20°, and about 25°. In additional embodiments, the pre-angle abutment can be at an angle between about 5° to about 45°, about 10° to about 40°, about 15° to about 35°, and about 20° to about 30°. By way of example, the 20° pre-angled abutment, together with the range of divergence, allows a divergence up to about 40° of the cap 80 relative to the first and second cylindrical portions 252 and 254, respectively, of the abutment 200'. Illustratively, the range of divergence of the cap 20 is about 20°, about 21°, about 22°, about 23°, about 24°, about 25°, about 26°, about 27°, about 28°, about 29°, about 30°, about 31°, about 32°, about 33°, about 34°, about 35°, about 36°, about 37°, about 38°, about 39°, and about 40° relative to the 20° pre-angled abutment 200".

Figures 42, 43:
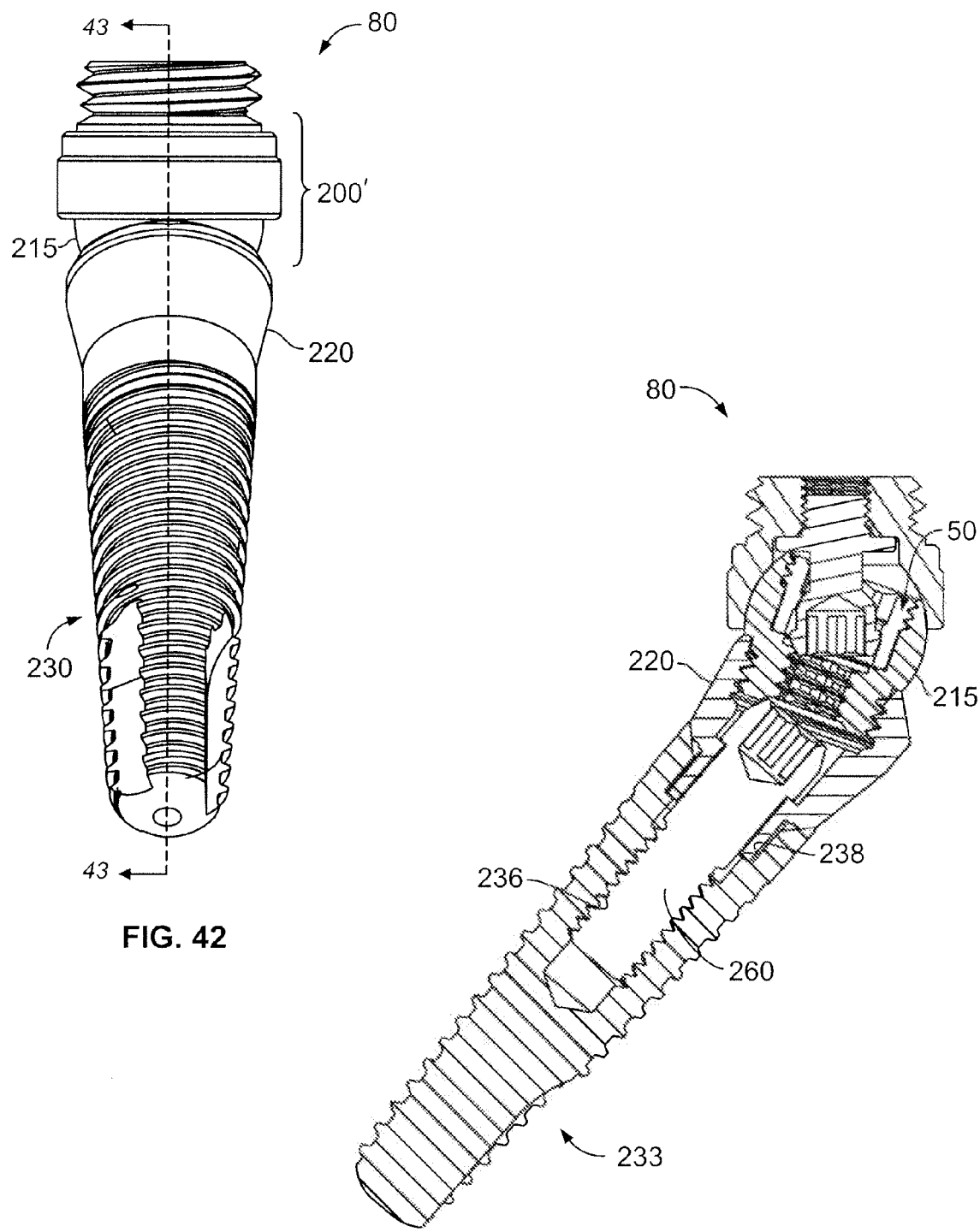
FIG. 42 is a perspective view of the assembled dental attachment device with a 20° pre-angled abutment of FIG. 40
FIG. 43 is a cross-sectional view of FIG. 42.

The two-piece pre-angled abutment 200" can be assembled and secured in an implant 233 using a retaining screw 260 as shown in FIGS. 42 and 43. The attachment portion 225 of the second component 220 is fitted into cavity 238 of the implant 233. The retaining screw 260 is set through the through bore 239 and screwed into the threaded bore 236, thereby securing the second component 220 to the implant 230. The threaded shaft 227 of the first component 215 is engaged and secured into the threaded portion 251 of the cavity 236 of the second component 220.

In another embodiment, the dental attachment device 10 comprises a cap 80 for securing the dental appliance (not shown) and an abutment 20 for attachment to a non-vital tooth root, implant or the like. The cap 80 is positioned over and engaged with abutment 20 providing a metal-to-metal engagement of the inner concave surface 92 of wall 90 over the convex outer surface 35 of the abutment 20. The mating of these two surfaces results in a galling or press fit effect that creates retentive force between the components and secures the cap 80 to the abutment 20. The metal-to-metal interference and resulting retention is achieved by the compressive biting force applied at the time of seating the prosthesis and caps on the abutments and then further through the continuous mastication forces imparted by the patient.

Another embodiment of the abutments disclosed herein is incorporated as a mini implant for osseo-integration into the jawbone of a subject. A mini implant is a small-diameter, one-piece root form implant that osseo-integrates into the jawbone and allows immediate loading of a dental appliance. The mini implant come in a number of different sizes. The shaft may range in diameter from about 1.8 mm to about 2.9 mm. Illustratively, the diameter of the shaft may be about 1.8 mm, about 1.9 mm, about 2.0 mm, about 2.1 mm, about 2.2 mm, about 2.3 mm, about 2.4 mm, about 2.5 mm, about 2.6 mm, about 2.7 mm, about 2.8 mm and about 2.9 mm. Further, the length of the shaft ranges from about 10 mm to about 18 mm. In further embodiments, the length may be about 10 mm, about 11 mm, about 12 mm, about 13 mm, about 14 mm, about 15 mm, about 16 mm, about 17 mm, and about 18 mm.

FIGS. 44 to 46 illustrate one embodiment of a healing cap 300. The healing cap 300 comprises an upper surface 310 that is generally flat and an annular skirt 320 projecting downwardly from the upper surface 310 to surround a shaft 330. The shaft comprises a distal threaded portion 333 and a coaxial trunco-conical section 340. A tool-receiving bore 345 extends inwardly from the upper surface 310. The tool-receiving bore 345 can be, for example hexagonal with flat faces, for engagement by a suitable tool.

Figure 47:
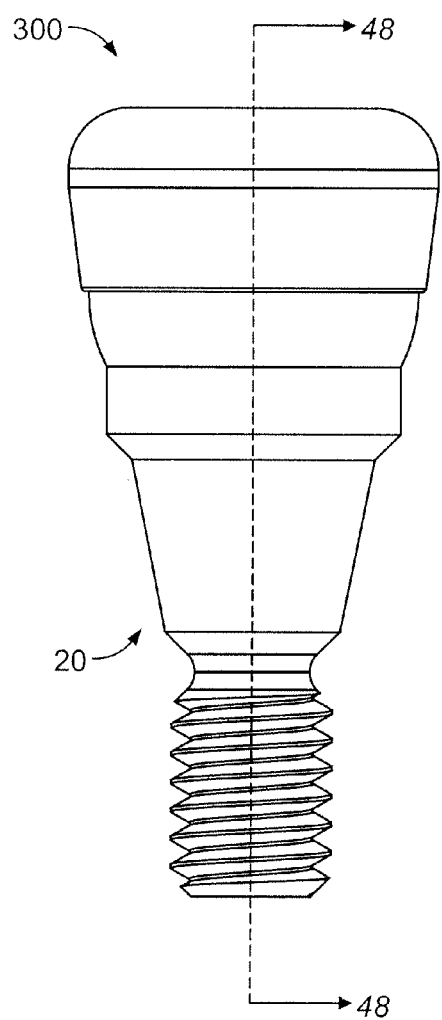
FIG. 47 is a side view of assembled healing cap on an abutment.
Figure 48:
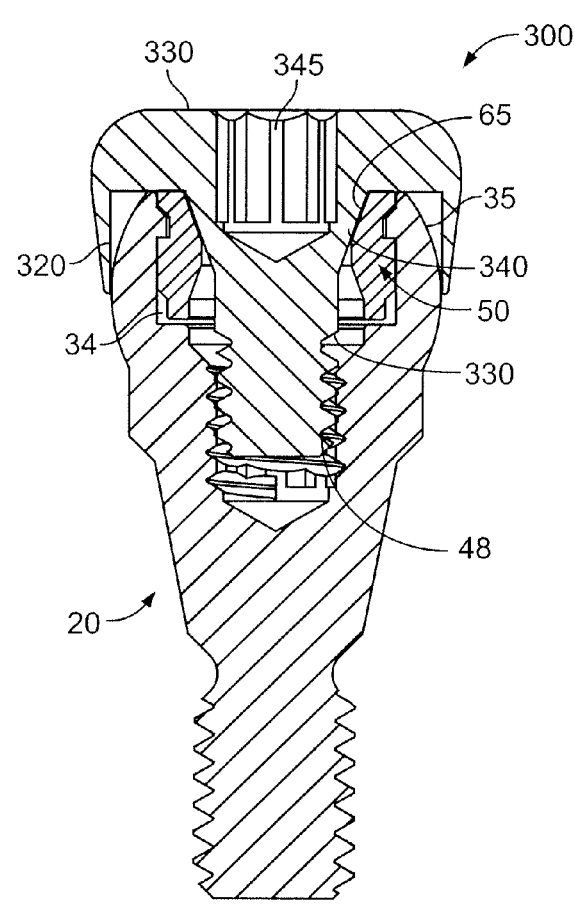
FIG. 48 is a cross-sectional view of FIG. 47.
Figure 49:
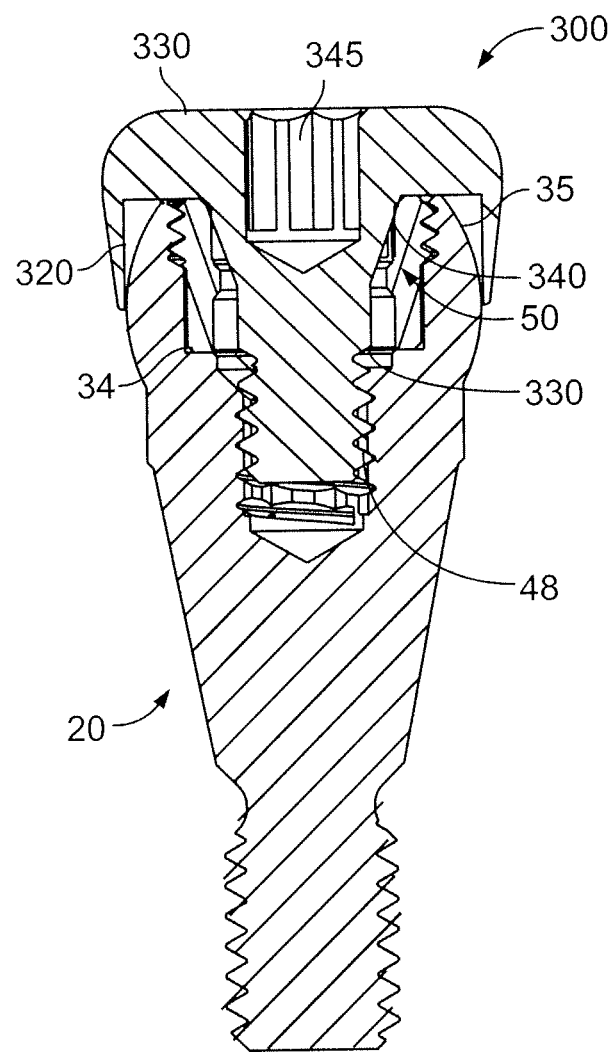
FIG. 49 is a cross-sectional view of an alternative embodiment of FIG. 47.

Referring to FIGS. 47 to 49, the healing cap 300 is positioned over the socket 34 of the abutment 20 and the shaft is engaged through the ring 50 and screwed into the threaded bore 48. The tapered inner surface 65 of the ring 50 matches the trunco-conical section 340 of the shaft 330 of the healing cap 300. At the same time, the annular skirt 320 is engaged and tightened over the outer surface 35 of the abutment 80. The fit between the healing cap 300 and abutment 20 can help to create a seal that minimizes the penetration of oral fluids into the abutment cavity in an effort to prevent microbial contamination. The healing cap 300 can be used with other embodiments of abutment 20 disclosed and/or contemplated herein.

Figure 50:
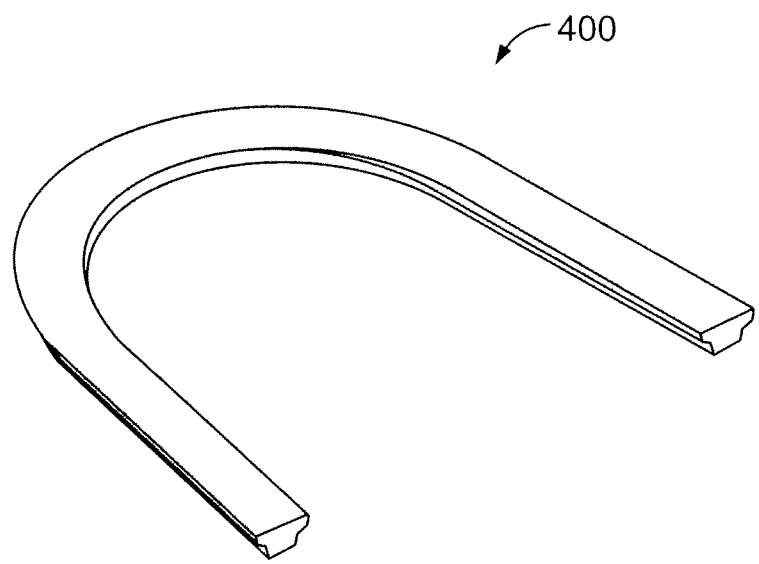
FIG. 50 is a perspective view of curved bar.
Figure 51:
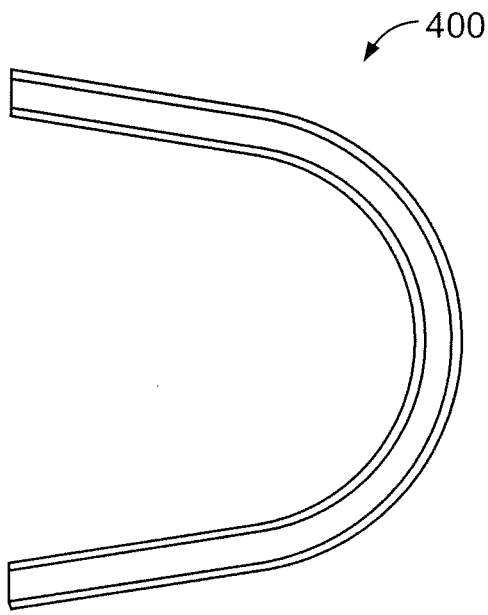
FIG. 51 is a top view of FIG. 49.

FIGS. 50 and 51 illustrates one embodiment of a curved bar attachment 400. The bar attachment 400 can be used to connect two or more dental attachment devices 10 to a rigid frame for a full denture, overdenture or partial denture. The bar 400 can be made in a number of different sizes to accommodate varying patients' dental arch, for example, small, medium, large, and extra large, and made of suitably strong material such as titanium, titanium alloys, cobalt-chromium-molybdenum alloys, stainless steel with a titanium nitride coating, zirconium, tantalum, gold, platinum, palladium, hafnium and tungsten, as well as other materials known to those of skill in the art. The bar may also be cut into partial arch shapes that are both straight and curved of various lengths.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein are representative of the subject matter which is broadly contemplated by the present invention. It is further understood that the scope of the present invention is not intended to be limited to the embodiment shown herein but is to be accorded the widest scope consistent with the patent law and the principles and novel features disclosed herein.

All references, including publications, patent applications, and patents, cited herein are hereby incorporated by reference to the same extent as if each reference were individually and specifically indicated to be incorporated by reference and were set forth in its entirety herein.

The use of the terms "a," "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

Alternative embodiments of the claimed disclosure are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

The invention claimed is:

1. A method for securing a dental appliance in a subject's mouth by a dental professional, comprising the steps of:
engaging a first, attachment portion of an abutment into an existing non-vital tooth root, implant, or intermediary abutment, a second portion of the abutment outside the non-vital tooth root, implant, or intermediary abutment having a convex outer surface and a socket having an open end facing away from the first, attachment portion;

retentively engaging a head portion of a one-piece removable ball through the open end of the socket with the head portion in swivel engagement in the socket, the removable ball having a shaft extending from the head portion and secured to a cap that is secured to or integral with a dental appliance; and retentively engaging a concave surface portion of the cap in face to face engagement over the convex outer surface of the abutment;

wherein the head portion is in swivel engagement in the socket during use of the dental appliance to allow a range of divergence between the cap and the abutment, and a retention force is provided by the retentive engagement of the removable ball into the abutment.

2. The method of claim 1, wherein the dental professional secures a plurality of abutments in the mouth of the subject.

3. The method of claim 2, wherein the retention force varies between and among the plurality of abutments and removable balls.

4. The method of claim 1, wherein the head portion comprises a surface feature selected from the group consisting of a barb, an annular edge, a partially annular edge, and a lip.

5. The method of claim 1, wherein the retention force is about 15 to about 75 pounds.

6. The method of claim 5, wherein the retention force is about 30 to 40 pounds.

7. The method of claim 1, wherein the concave inner surface portion is metal and the convex outer surface of the abutment is metal.

8. The method of claim 1, wherein the retentive engagement of the concave inner surface portion of the cap over the convex outer surface of the abutment creates a press fit between the concave inner surface portion and the convex outer surface.

9. The method of claim 1, wherein the retentive engagement of the concave inner surface portion of the cap over the convex outer surface of the abutment creates a seal which prevents fluids from entering the open end of the abutment.

10. The method of claim 1, wherein the retentive engagement of the head portion of the removable ball into the open end of the abutment includes a gap between the cap and the abutment which allows the cap to pivot relative to the abutment.

11. The method of claim 1, further comprising threadably securing a threaded upper end portion of the shaft into the cap.

12. A method for securing a dental appliance in a subject's mouth by a dental professional, comprising the steps of:

engaging a first, attachment portion of an abutment into an existing non-vital tooth root, implant, or intermediary abutment, a second portion of the abutment outside the non-vital tooth root, implant, or intermediary abutment having a convex outer surface and a socket having an open end facing away from the first, attachment portion;

positioning a ring through the open end and into the socket of the abutment;

retentively engaging a head portion of a one-piece removable ball through the open end of the socket with the head portion in swivel engagement with the ring, the removable ball having an integral shaft extending from the head portion and secured to or integral with a cap that is secured to or integral with a dental appliance;

retentively engaging a concave inner surface portion of the cap in face to face engagement over the convex outer surface of the abutment.

13. The method of claim 12, wherein the ring is made of a plastic material.

14. The method of claim 13, wherein the ring is made of a polyether ether ketone (PEEK) material.

15. The method of claim 12, wherein the ring is threadedly secured into the abutment.

* * * * *